(12) United States Patent
Cherkaoui et al.

(10) Patent No.: US 6,630,076 B1
(45) Date of Patent: Oct. 7, 2003

(54) LIQUID CRYSTALLINE COMPOUNDS

(75) Inventors: Zoubair Mohammed Cherkaoui, Allschwil (CH); Carsten Benecke, Weil am Rhein (DE)

(73) Assignee: Rolic AG, Zug (CH)

( * ) Notice: Subject to any disclaimer, the term of this patent is extended or adjusted under 35 U.S.C. 154(b) by 0 days.

(21) Appl. No.: 09/762,332

(22) PCT Filed: Aug. 9, 1999

(86) PCT No.: PCT/IB99/01419

§ 371 (c)(1),
(2), (4) Date: Apr. 10, 2001

(87) PCT Pub. No.: WO00/07975

PCT Pub. Date: Feb. 17, 2000

(30) Foreign Application Priority Data

Aug. 7, 1998 (GB) .............................................. 9817272

(51) Int. Cl.$^7$ .............................................. C09K 19/52
(52) U.S. Cl. .............................. 252/299.01; 252/299.61
(58) Field of Search ........................... 252/299.9, 299.1, 252/299.2, 299.3, 299.4, 299.5, 299.6, 299.61, 299.62, 299.63, 299.64, 299.65, 299.66, 299.67, 299.68, 299.7

(56) References Cited

U.S. PATENT DOCUMENTS

| | | | |
|---|---|---|---|
| 3,971,824 A | 7/1976 | Van Meter et al. | |
| 5,567,349 A | 10/1996 | Kelly et al. | |
| 5,593,617 A | 1/1997 | Kelly et al. | |
| 5,707,544 A | 1/1998 | Kelly | |

FOREIGN PATENT DOCUMENTS

| | | |
|---|---|---|
| EP | 0 675 186 | 10/1995 |
| EP | 0 700 981 | 3/1996 |
| EP | 0 748 852 | 12/1996 |

Primary Examiner—Mark F. Huff
Assistant Examiner—Jennifer R. Sadula
(74) Attorney, Agent, or Firm—Finnegan, Henderson, Farabow, Garrett & Dunner, LLP

(57) ABSTRACT

A compound of formula (I): wherein $MG^1$ and $MG^3$ each independently represent an optionally-substituted aliphatic group with 1 to 80 C-atoms, in which one or more C-atoms may be replaced by a heteroatom, in such a way that oxygen atoms are not linked to one another; or an optionally-substituted aromatic or non-aromatic carbocyclic or heterocyclic ring system, with 1 to 80 C-atoms; and $MG^2$ represents a group comprising at least two and up to four optionally-substituted aromatic or non-aromatic carbocyclic or heterocyclic ring systems, with 1 to 80 C-atoms, wherein, when $MG^2$ represents a group comprising four optionally-substituted ring systems, at least three of the ring systems are aligned in between $B^1$ and $B^2$. The groups $MG^1$, $MG^2$ and $MG^3$ in these new "staircase molecules" may be selected so that each one has one or more of the properties which are required in an LCP material prepared by polymerizing the compound.

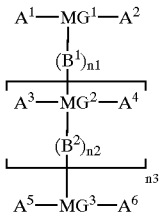

(I)

26 Claims, No Drawings

LIQUID CRYSTALLINE COMPOUNDS

The invention relates to new liquid crystalline compounds, mixtures of those compounds and their application in optical devices. More particularly, it relates to the use of a component of a polymerisable liquid crystalline mixture in the production of orientated liquid crystalline polymers; compounds used as components in polymerisable liquid crystalline mixtures; liquid crystalline mixtures comprising these components, liquid crystalline polymers prepared from such components; and liquid crystalline devices comprising those compounds.

Liquid crystal polymers (LCPs) are used in the manufacture of optical components such as waveguides, optical gratings, filters, retarders, piezoelectric cells and non-linear optical cells and films. The choice of LCP for use in any one of the aforementioned optical components depends upon its associated optical properties such as the optical anisotropy, refractive index, transparency and dispersion. Optical filters, for example, contain LCPs having a large anisotropy ($\Delta n$) and a low dispersion ($n=f(\lambda)$).

In some applications there is a requirement to produce LCPs in which the component molecules adopt a specific tilt angle or orientation with respect to the plane of the substrate or to a plane perpendicular to the substrate. These LCP materials can be used as optical components such as compensation layers and retarders. Such optical components may be used in the production of liquid crystal devices (LCDs) with improved viewing angles, for example.

LCPs are manufactured by orientating a layer of a polymerisable liquid crystal single compound or mixture on an orientated substrate and cross-linking the mesogenic layer to form a liquid crystal polymer (LCP) network. Polymerisable LC compounds used in the manufacture of the LCPs need to be chemically and thermally stable, stable to electromagnetic radiation, soluble in standard solvents and miscible with other LC components, and to exhibit liquid crystalline properties over the range 25 to 150° C., preferably 25 to 80° C. The configuration imposed by the orientation layer on the polymerisable LC single compound or mixture becomes fixed or frozen into the LCP network formed upon cross-linking. The resulting LCP films have a high viscosity and are stable to mechanical stresses, temperature and light exposure.

There is therefore a need for a liquid crystalline single compound or mixture which exhibits a broad liquid-crystalline thermal range and which can be orientated on a substrate prior to cross-linking in such a way that the orientation of the LC single compound or mixture on the substrate remains stable over the period required for manufacturing the LCP network. Components which may be used in photo-crosslinkable liquid crystalline layers are particularly desirable.

Compounds known from the prior art include those disclosed in EP-A-0675186, EP-A-0700981 and EP-A-0748852 (all F. Hoffmann-La Roche A G). The three earlier documents disclose compounds such as (taken from EP-A-0675186):

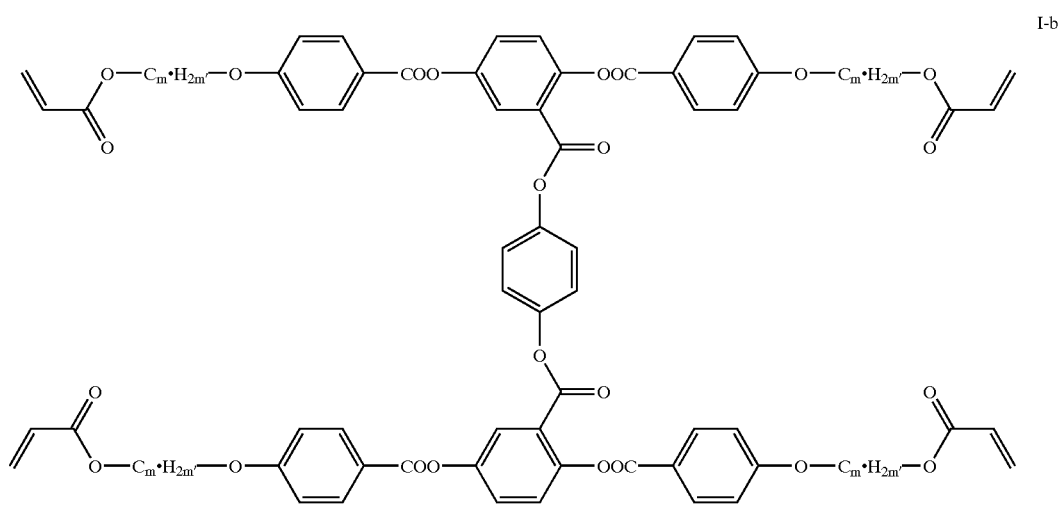

I-b

U.S. Pat. No. 3,971,824 (Van Meter et al./Eastman Kodak Company) discloses in its broadest aspect compounds of the following formula:

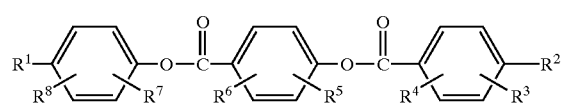

I.

though in fact there is no enabling disclosure of anything other than the following:

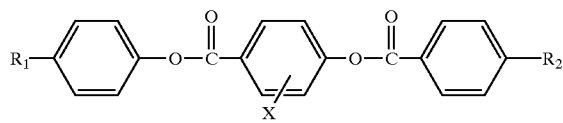

II.

where X is chlorine.

Previous strategies used for obtaining the desired thermal and optical properties with a given LCP material have mainly relied upon mixtures of compounds comprising at least one liquid crystalline polymerisable monomer and the combination of their individual properties. However due to the general incompatibility of the latter components at the molecular scale, the thermodynamic behaviour of their corresponding mixtures is generally undesirable (for example, a depression of the clearing point, a reduction of the liquid crystalline range etc.), besides some problems of miscibility between the different components of the mixture leading to difficulties in achieving a uniform orientation of the LCP material. To ameliorate this situation, a new concept of obtaining LCP materials of special thermal and optical properties was investigated. This concept uses chemical junctions at lateral positions of different molecules, at least one of them being mesogenic, having each one or more of the properties which are required in the final LCP material. Depending on the application, these properties can be selectively induced from at least one of the mesogenic stairs of the new "staircase molecules".

Thus the invention provides chiral or achiral "staircase" compounds of formula I:

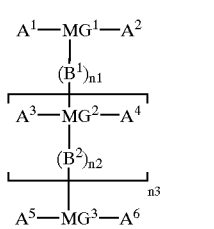

(I)

wherein:
- $A^1$ to $A^6$ each independently represent hydrogen; an optionally-substituted methyl group; or an optionally-substituted hydrocarbon group of 2 to 80 C-atoms, in which one or more C-atoms may be replaced by a heteroatom, in such a way that oxygen atoms are not linked to one another;
- $B^1$ and $B^2$ each independently represent a single bond, an oxygen atom or an optionally-substituted hydrocarbon group of 1 to 80 C-atoms, in which one or more C-atoms may be replaced by a heteroatom, in such a way that oxygen atoms are not linked to one another;
- $MG^1$ and $MG^3$ each independently represent an optionally-substituted aliphatic group with 1 to 80 C-atoms, in which one or more C-atoms may be replaced by a heteroatom, in such a way that oxygen atoms are not linked to one another; or an optionally-substituted aromatic or non-aromatic carbocyclic or heterocyclic ring system; with 1 to 80 C-atoms;
- $MG^2$ represents a group comprising at least two and up to four optionally-substituted aromatic or non-aromatic carbocyclic or heterocyclic ring systems, with 1 to 80 C-atoms, wherein, when $MG^2$ represents a group comprising four optionally-substituted ring systems, at least three of the ring systems are aligned in between $B^1$ and $B^2$;
- n1 and n2 are each independently 1 or 2, where "n1=2" (or "n2=2") indicates the presence of two separate linkages via the groups $B^1$ (or the groups $B^2$) between the groups $MG^1$ and $MG^2$ (or $MG^2$ and $MG^3$); and
- n3 is a positive integer up to 1000;

with the proviso that:
- when $A^3$ and $A^4$ both represent hydrogen, then both $MG^1$ and $MG^3$ represent an araliphatic group with 1 to 80 C-atoms, in which one or more C-atoms may be replaced by a heteroatom, or an optionally-substituted aromatic or non-aromatic carbocyclic or heterocyclic ring system, with 1 to 80 C-atoms; and at least two of $A^1$, $A^2$, $A^5$ and $A^6$ each independently represent an optionally-substituted hydrocarbon group of 3 to 80 C-atoms, in which one or more C-atoms may be replaced by a heteroatom;
- when $A^1$, $A^2$, $A^5$ and $A^6$ all represent hydrogen, then $A^3$ and $A^4$ both represent an optionally-substituted hydrocarbon group of 3 to 80 C-atoms, in which one or more C-atoms may be replaced by a heteroatom; and
- when $MG^2$ represents a group comprising two or three optionally-substituted ring systems, then neither of $A^3$ and $A^4$ includes an aromatic ring.

The term "aliphatic" includes straight-chain and branched alkylene, as well as saturated and unsaturated groups. Possible substituents include alkyl, aryl (thus giving an araliphatic group) and cycloalkyl, as well as amino, cyano, epoxy, halogen, hydroxy, nitro, oxo etc. Possible heteroatoms which may replace carbon atoms include nitrogen, oxygen and sulphur. In the case of nitrogen further substitution is possible with groups such as alkyl, aryl and cycloalkyl. Likewise, the terms "alkyl" and "alkylene", as used herein, includes straight-chain and branched groups, as well as saturated and unsaturated groups.

When $MG^2$ represents a group comprising four optionally-substituted ring systems, at least three of the ring systems are aligned in between $B^1$ and $B^2$. Thus, at least three of the rings are all in a discrete identifiable block positioned in between $B^1$ and $B^2$, not in an arbitrarily defined region with some of the rings protruding from the axis of the molecule connecting $B^1$ with $B^2$. Comparison may be made with compounds such as Compound I-a of EP-A-0675186:

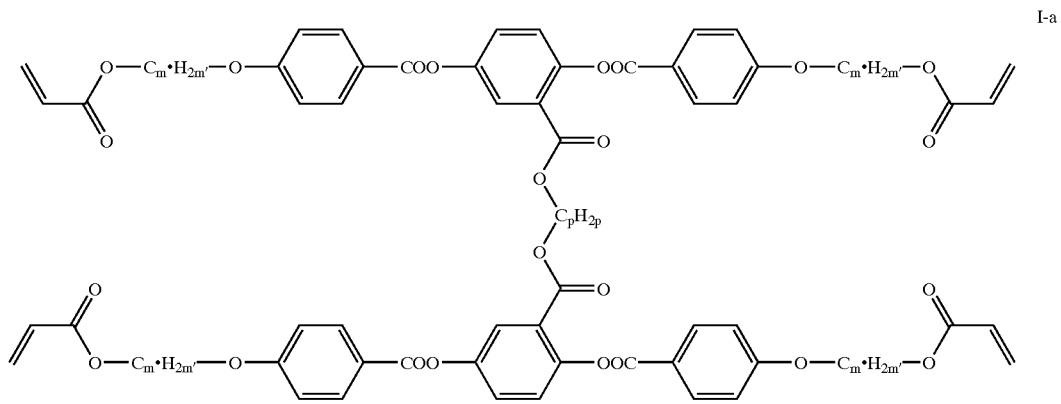

I-a which could be drawn with an arbitrarily defined Z-shaped central portion having four rings. Two of these rings protrude from the axis of the molecule connecting the remaining arms of the molecule, and the compound falls outside the scope of the present invention.

When $MG^2$ represents a group comprising two or three optionally-substituted ring systems, then neither of $A^3$ and $A^4$ includes an aromatic ring. This again makes it clear that with compounds such as Compound I-a of U.S. Pat. No. 5,567,349 fall outside the scope of the present invention. It is not possible to produce the present invention by arbitrarily labelling parts of molecules known from the prior art.

The groups $MG^1$, $MG^2$ and $MG^3$ in the new "staircase molecules" may be selected so that each has one or more of the properties which are required in the final LCP material. To an expert in liquid crystals, the molecular architecture of compounds of formula I would not have been thought to be favourable for obtaining a liquid crystalline mesophase, because a bulky substituent at a position lateral to a mesogenic core would have been thought to cause a loss of mesogenic character. However we have now discovered that the compounds of formula I were surprisingly found to be liquid crystalline over a broad thermal range. Besides, they are suitable for producing a high tilt and high optical birefringence together with well oriented LCP films.

$MG^2$ may be either a mesogenic group or otherwise.

It is advantageous for the liquid crystalline compounds to be photo-crosslinkable, so that for example they may be used in a crosslinked state in optical devices. Thus preferably at least one of $A^1$ to $A^6$ includes a polymerisable group. In such a case, when $A^3$ and $A^4$ both represent hydrogen then at least one of $A^1$, $A^2$, $A^5$ and $A^6$ would include a polymerisable group; whereas when $A^1$, $A^2$, $A^5$ and $A^6$ all represent hydrogen then at least one of $A^3$ and $A^4$ would include a polymerisable group.

In a first preferred embodiment of the present invention, each or any of the groups $A^1$ to $A^6$ may be selected from a residue of formula (II):

$$P-(Sp^1)_{k1}-(X^1)_{t1}- \qquad (II)$$

wherein:

P is hydrogen or a polymerisable group selected from groups comprising $CH_2=CW-$, $CH_2=W-O-$, $CH_2=CW-COO-$, $CH_2=C(Ph)-COO-$, $CH_2=CH-COO-Ph-$, $CH_2=CW-CO-NH-$, $CH_2=C(Ph)-CONH-$, $CH_2=C(COOR')-CH_2-COO-$, $CH_2=CH-O-$, $CH_2=CH-OOC-$, $(Ph)-CH=CH-$, $CH_3-C=N-(CH_2)_{m3}-$, $HO-$, $HS-$, $HO-(CH_2)_{m3}-$, $HS-(CH_2)_{m3}-$, $HO(CH_2)_{m3}COO-$, $HS(CH_2)_{m3}COO-$, $HWN-$, $HOC(O)-$, $CH_2=CH-Ph-(O)_{m4}$

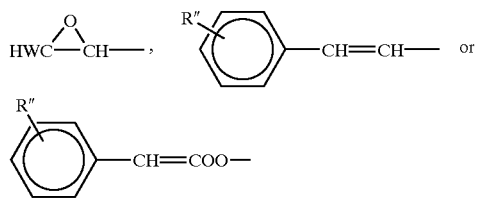

wherein:

W represents H, F, Cl, Br or I or a $C_{1-5}$ alkyl group;
m3 is an integer having a value of from 1 to 9;
m4 is an integer having a value of 0 or 1,
R' represents a $C_{1-5}$ alkyl group; and R" represents a $C_{1-5}$ alkyl group, methoxy, cyano, F, Cl, Br or I;

$Sp^1$ represents an optionally-substituted $C_{1-20}$ alkylene group, in which one or more C-atoms may be replaced by a heteroatom;

$k^1$ is an integer having a value of from 0 to 4;

$X^1$ represents $-O-$, $-S-$, $-NH-$, $N(CH_3)-$, $-CH(OH)-$, $-CO-$, $-CH_2(CO)-$, $-SO-$, $-CH_2(SO)-$, $-SO_2-$, $-CH_2(SO_2)-$, $-COO-$, $-OCO-$, $-OCO-O-$, $-S-CO-$, $-CO-S-$, $-SOO-$, $-OSO-$, $-SOS-$, $-CH_2-CH_2-$, $-OCH_2-$, $-CH_2O-$, $-CH=CH-$, or $-C\equiv C-$; and $t^1$ is an integer having a value of 0 or 1;

with the proviso that at least one of the groups $A^1$ to $A^6$ is not a hydrogen atom.

In relation to the residue of formula (II), the term Ph is to be understood as denoting phenylene and (Ph) as denoting phenyl.

The $C_{1-20}$ alkylene group $Sp^1$ may comprise branched or straight chain alkylene groups and may be unsubstituted, mono- or polysubstituted by F, Cl, Br, I or CN. Alternatively or in addition one or more of $CH_2$ groups present in the hydrocarbon chain may be replaced, independently, by one or more groups selected from $-O-$, $-S-$, $-NH-$, $N(CH_3)-$, $-CH(OH)-$, $-CO-$, $-CH_2(CO)-$, $-SO-$, $-CH_2(SO)-$, $-SO_2-$, $-CH_2(SO_2)-$, $-COO-$, $-OCO-$, $-OCO-O-$, $-S-CO-$, $-CO-S-$, $-SOO-$, $-OSO-$, $-SOS-$, $-C\equiv C-$, $-(CF_2)-_r$, $-(CD_2)_s-$ or $C(W^1)=C(W^2)-$, with the proviso that no two oxygen atoms are directly linked to each other. $W^1$ and $W^2$ each represent, independently, H, $H-(CH_2)_{q1}-$ or Cl. The integers r, s and q1 each independently represent a number of between 1 and 15.

More preferably, $A^1$ to $A^2$ each independently represent a group of formula (III):

$$P^2-Sp^5-X^4- \qquad (III);$$

wherein:

$X^4$ represents $-O-$, $-CO-$, $-COO-$, $-OCO-$, $-C\equiv C-$, or a single bond, especially $-O-$, $-COO-$, $-OCO-$ or single bond;

$Sp^5$ represents a $C_{1-20}$ straight-chain alkylene group, especially ethylene, propylene, butylene, pentylene, hexylene, heptylene, octylene, nonylene, decylene, undecylene, or dodecylene; and $P^2$ represents hydrogen, $CH_2=CW^5-$ or $CH_2=CW^5-(CO)_{v2}O-$, wherein:

$W^5$ represents H, $CH_3$, F, Cl, Br or I; and
v2 is 0 or 1.

One or more of $A^1$ to $A^6$ may also represent a $C_1-C_{20}$-alkyl, $C_1-C_{20}$-alkoxy, $C_1-C_{20}$-alkoxycarbonyl, $C_1-C_{20}$-alkylcarbonyl or $C_1-C_{20}$-alkylcarbonyloxy group, for example methyl, ethyl, propyl, butyl, pentyl, hexyl, heptyl, octyl, nonyl, decyl, undecyl, dodecyl, methoxy, ethoxy, n-propoxy, isopropoxy, butoxy, pentyloxy, hexyloxy, heptyloxy, octyloxy, nonyloxy, decyloxy, undecyloxy, dodecyloxy, methoxycarbonyl, ethoxycarbonyl, propoxycarbonyl, butoxycarbonyl, pentyloxycarbonyl, hexyloxycarbonyl, octyloxycarbonyl, nonyloxycarbonyl, decyloxycarbonyl, undecyloxycarbonyl, dodecyloxycarbonyl, acetyl, propionyl, butyryl, valeryl, hexanoyl, heptanoyl, octanoyl, nonanoyl, decanoyl, undecanoyl, dodecanoyl, terdecanoyl, acetoxy,

propionyloxy, butyryloxy, valeryloxy, hexanoyloxy, heptanoyloxy, octanoyloxy, nonanoyloxy, decanoyloxy, undecanoyloxy, dodecanoyloxy, terdecanoyloxy and the like.

In a second preferred embodiment of the present invention each or either of the groups $B^1$ and/or $B^2$ comprises a group of formula (IV):

$$(X^2)_{t2}—(Sp^2)_{k2}—(X^3)_{t3} \quad (IV)$$

wherein:
- $Sp^2$ represents a $C_{1-20}$ alkylene group;
- $X^2$ and $X^3$ each independently represent —O—, —S—, —NH—, N(CH$_3$)—, —CH(OH)—, —CO—, —CH$_2$(CO)—, —SO—, —CH$_2$(SO)—, —SO$_2$—, —CH$_2$(SO$_2$)—, —COO—, —OCO—, —OCO—O—, —S—CO—, —CO—S—, —SOO—, —OSO—, —SOS—, —CH$_2$—CH$_2$—, —OCH$_2$—, —CH$_2$O—, —CH=CH—, —C≡C— or a single bond;
- $k^2$ is an integer, having a value of 0 or 1;
- $t^2$ and $t^3$ are integers, each independently having a value of 0 or 1;

with the proviso that oxygen atoms are not linked one to another.

Preferably $B^1$ and $B^2$ each independently represent a group of formula (IV), wherein:
- $X^2$ to $X^3$ each independently represent —O—, —CO—, —COO—, —OCO—, —C≡C—, or a single bond, especially —O—, —COO—, —OCO— or a single bond; and
- $Sp^2$ represents a $C_{1-20}$ straight-chain alkylene group, especially ethylene, propylene, butylene, pentylene, hexylene, heptylene, octylene, nonylene, decylene, undecylene or dodecylene.

An especially preferred compound is that in which $B^1$ and $B^2$ each independently represent a group of formula (IV) and $A^1$ to $A^6$ each independently represent a group of formula (III).

The invention is particularly useful when $MG^2$ is a mesogenic group and the groups of $MG^1$ and $MG^3$ also impart mesogenic properties to the molecule, in addition to those properties imparted by the mesogenic group $MG^2$. Thus preferably $MG^2$ and at least one of $MG^1$ and $MG^3$ represents a mesogenic group comprising at least two optionally-substituted aromatic or non-aromatic carbocyclic or heterocyclic ring systems.

Preferably $MG^2$ represents a mesogenic group comprising 2 to 4 aromatic or non-aromatic carbocyclic or heterocyclic ring systems and optionally up to 3 bridging groups, and at least one of $MG^1$ and $MG^3$ represent a mesogenic group comprising 1 to 4 aromatic or non-aromatic carbocyclic or heterocyclic ring systems and optionally up to 3 bridging groups. These are more preferably selected from the meanings of formulae V:

$$C^1—(Z^1—C^2)_{a1}—(Z^2—C^3)_{a2}—(Z^3—C^4)_{a3} \quad (V),$$

in which:
- $C^1$ to $C^4$ are in each case independently optionally-substituted non-aromatic, aromatic, carbocyclic or heterocyclic groups;
- $Z^1$ to $Z^3$ are independently from each other —COO—, —OCO—, —CH$_2$—CH$_2$—, —OCH$_2$—, —CH$_2$O—, —CH=CH—, —Ch≡C—, —CH=CH—COO—, —OCO—CH=CH— or a single bond; and
- a1, a2 and a3 are independently integers 0 to 3, such that a1+a2+a3≤3.

Especially preferred are those in which $C^1$ to $C^4$ are selected from:

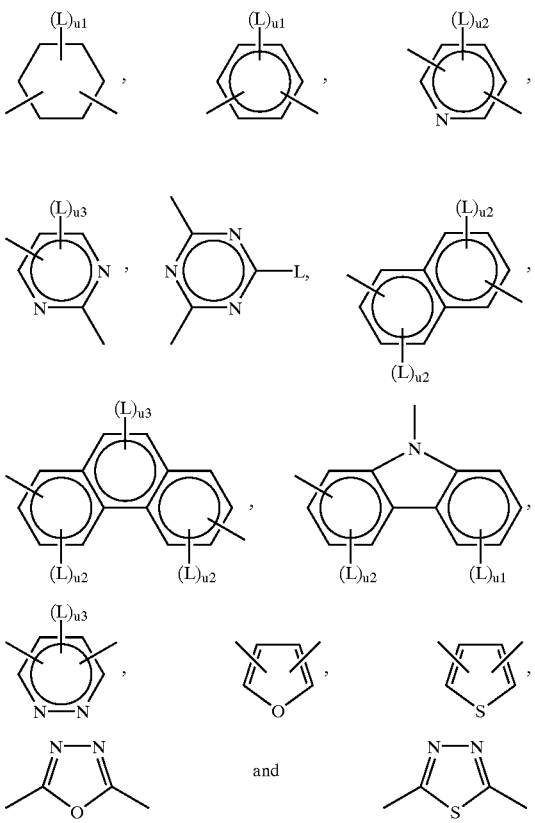

with:

L being —CH$_3$, —COCH$_3$, —NO$_2$, CN, or halogen u1 being 0, 1, 2, 3, or 4, u2 being 0, 1, 2, or 3, and u3 being 0, 1, or 2.

More especially preferred are those in which $C^1$ to $C^4$ are selected from cyclohexylene, phenylene, naphthylene or phenanthrylene.

For ease of synthesis, the molecules may possess some symmetrical aspects. Thus:

$A^1$ and $A^2$ may be identical;

$A^5$ and $A^6$ may be identical;

$A^1$—$MG^1$—$A^2$ and $A^5$—$MG^3$—$A^6$ may be identical;

$A^3$ and $A^4$ may be identical; or n1, n2 and n3 may equal 1 and $B^1$ and $B^2$ may be identical.

The compounds of the invention may be readily prepared using methods that are well known to the person skilled in the art, such as those documented in Houben-Weyl, *Methoden der Organischen Chemie*, Thieme-Verlag, Stuttgart. The compounds may for example be made according to the following reaction schemes:

Scheme 1:
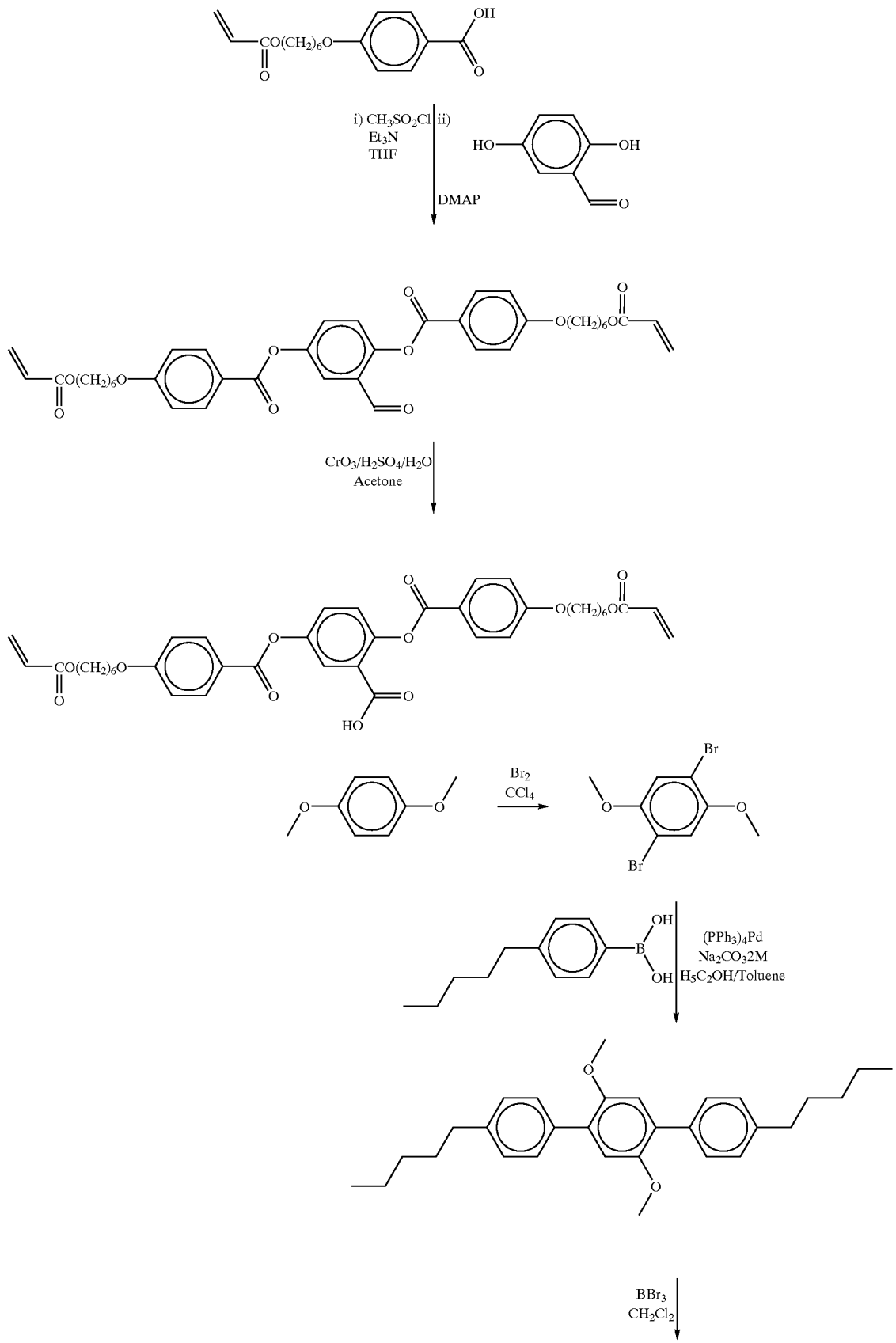

-continued
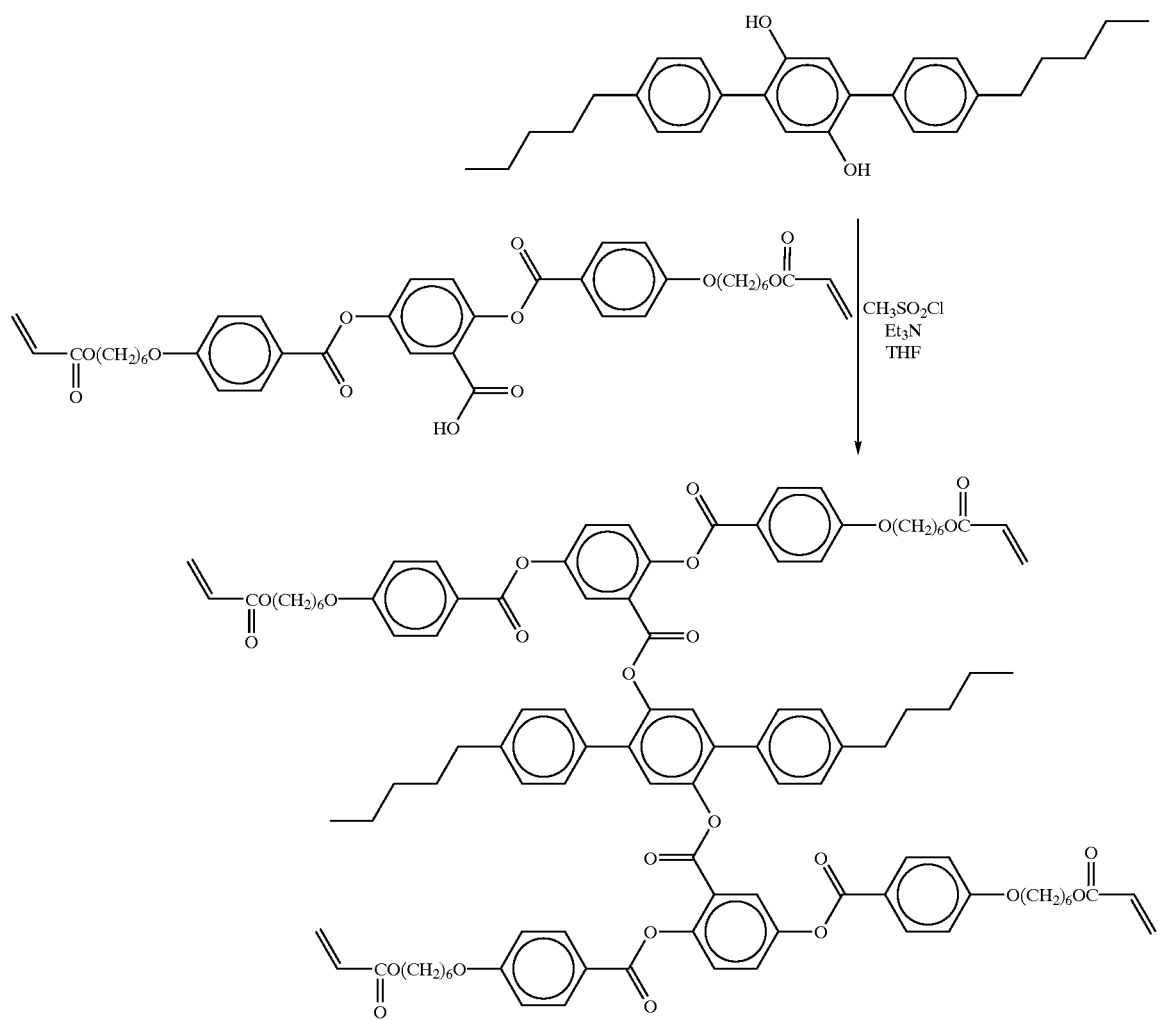
Scheme 2:
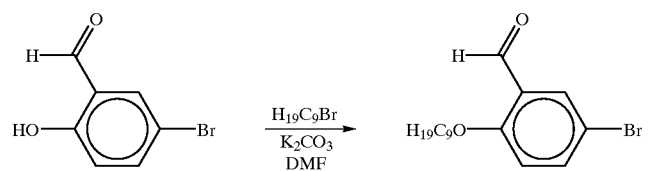
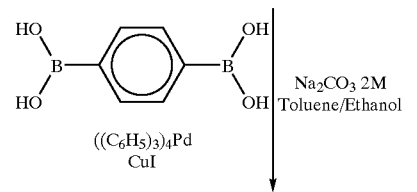

-continued
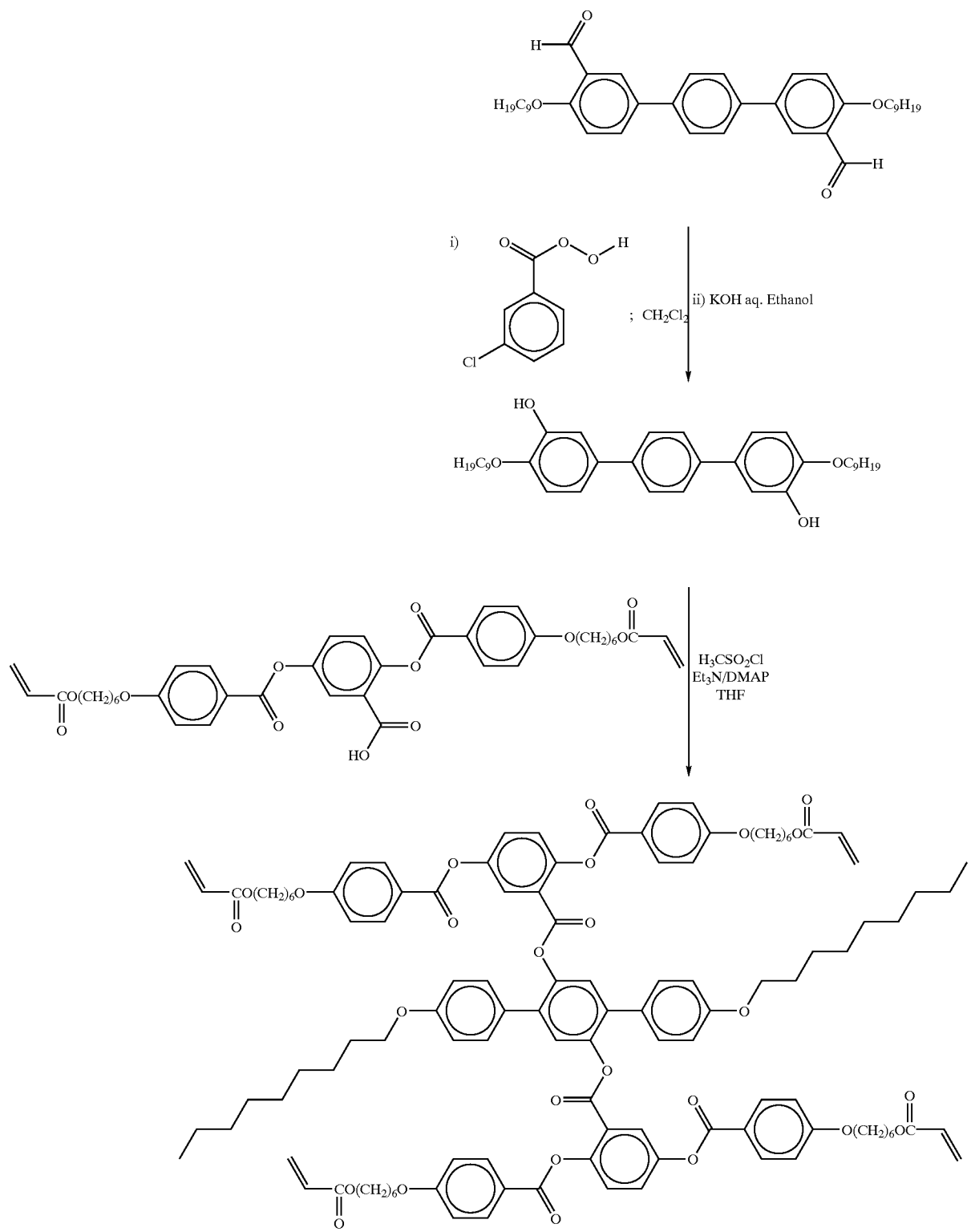

Scheme 3:
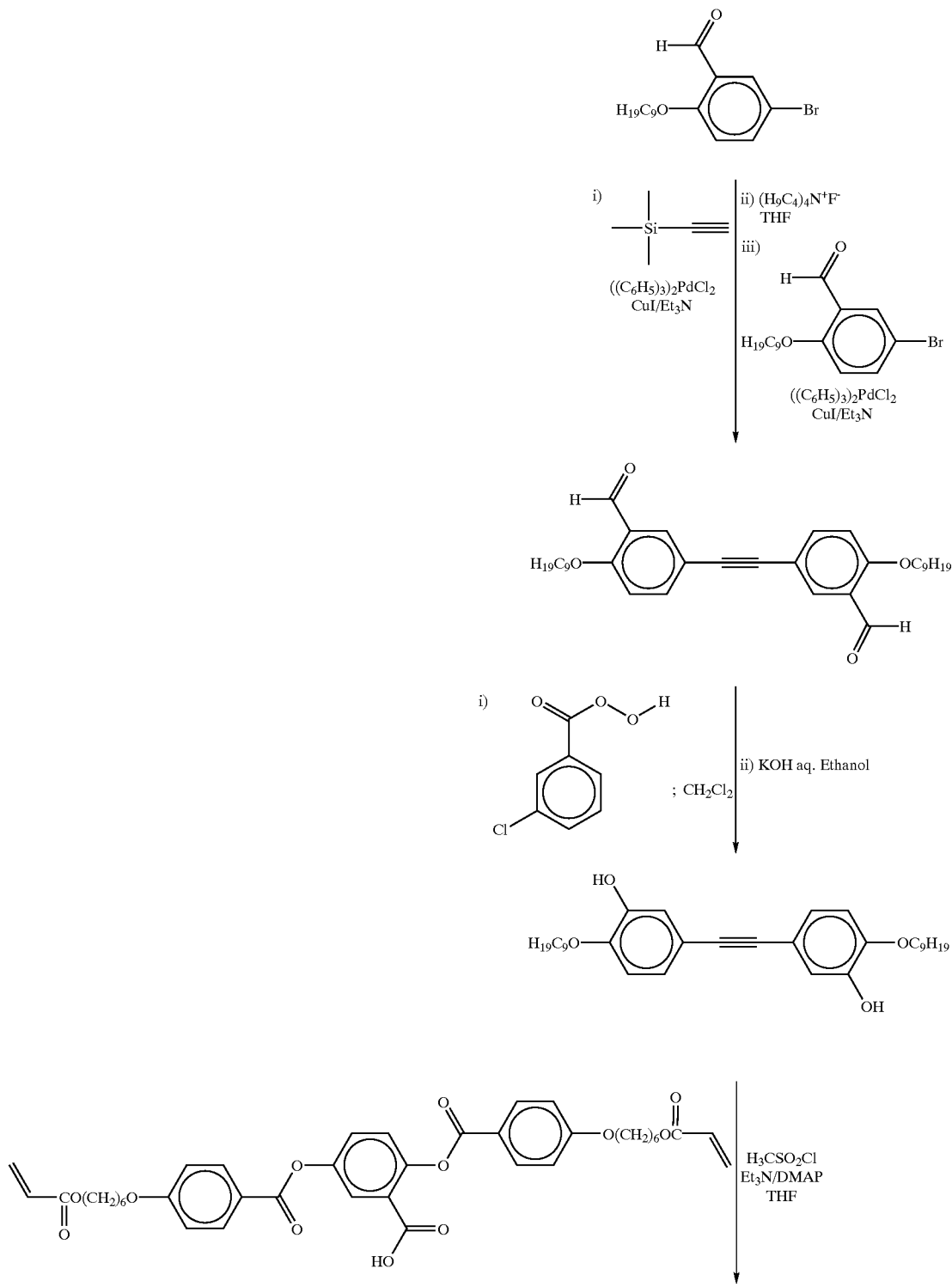

-continued
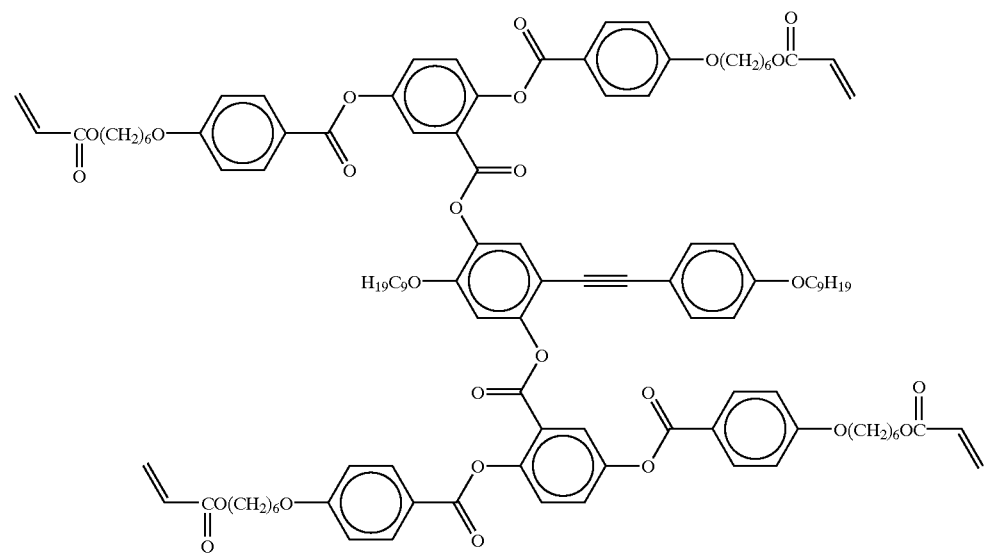
Scheme 4:
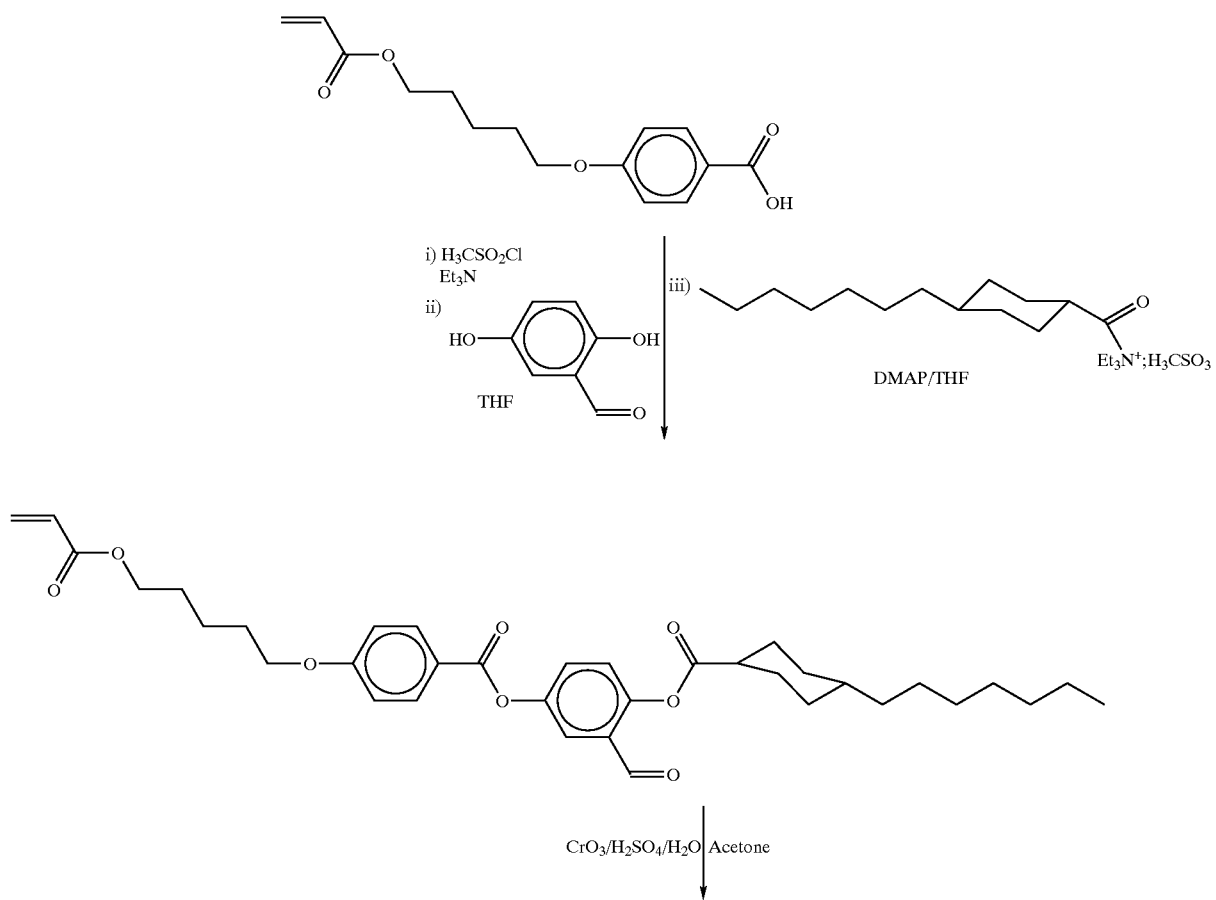

-continued
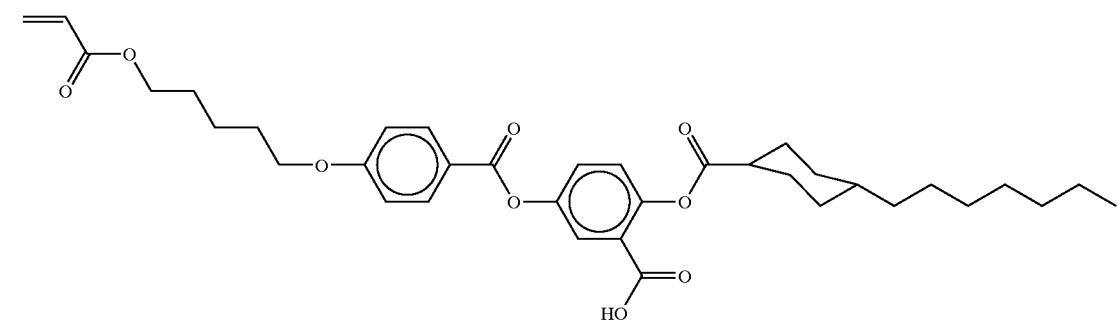
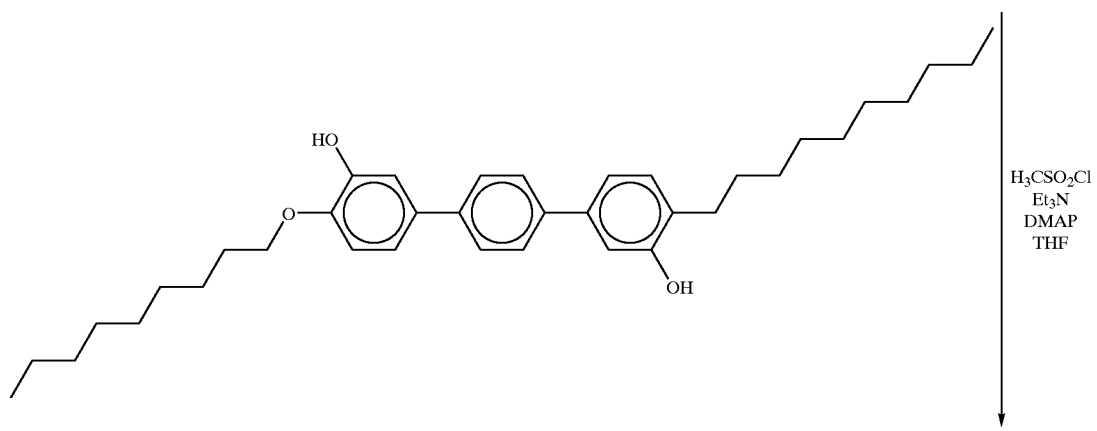
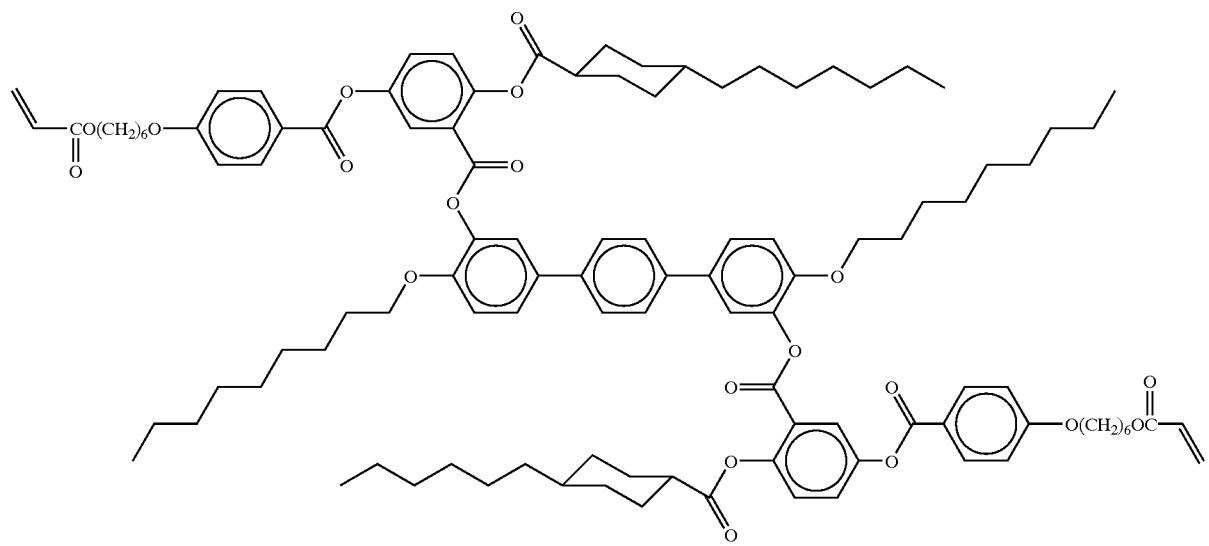

Scheme 5:
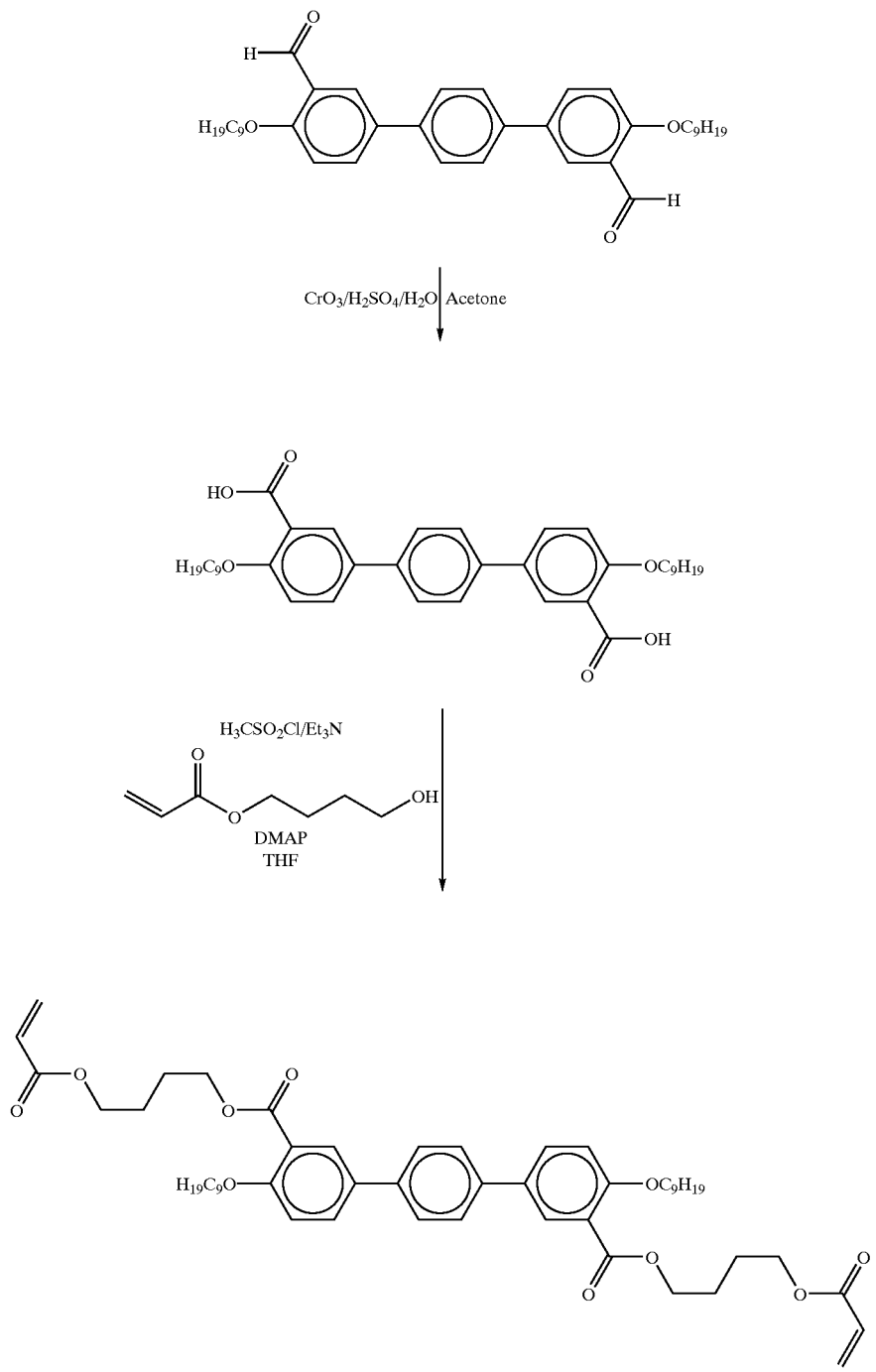

Scheme 6:
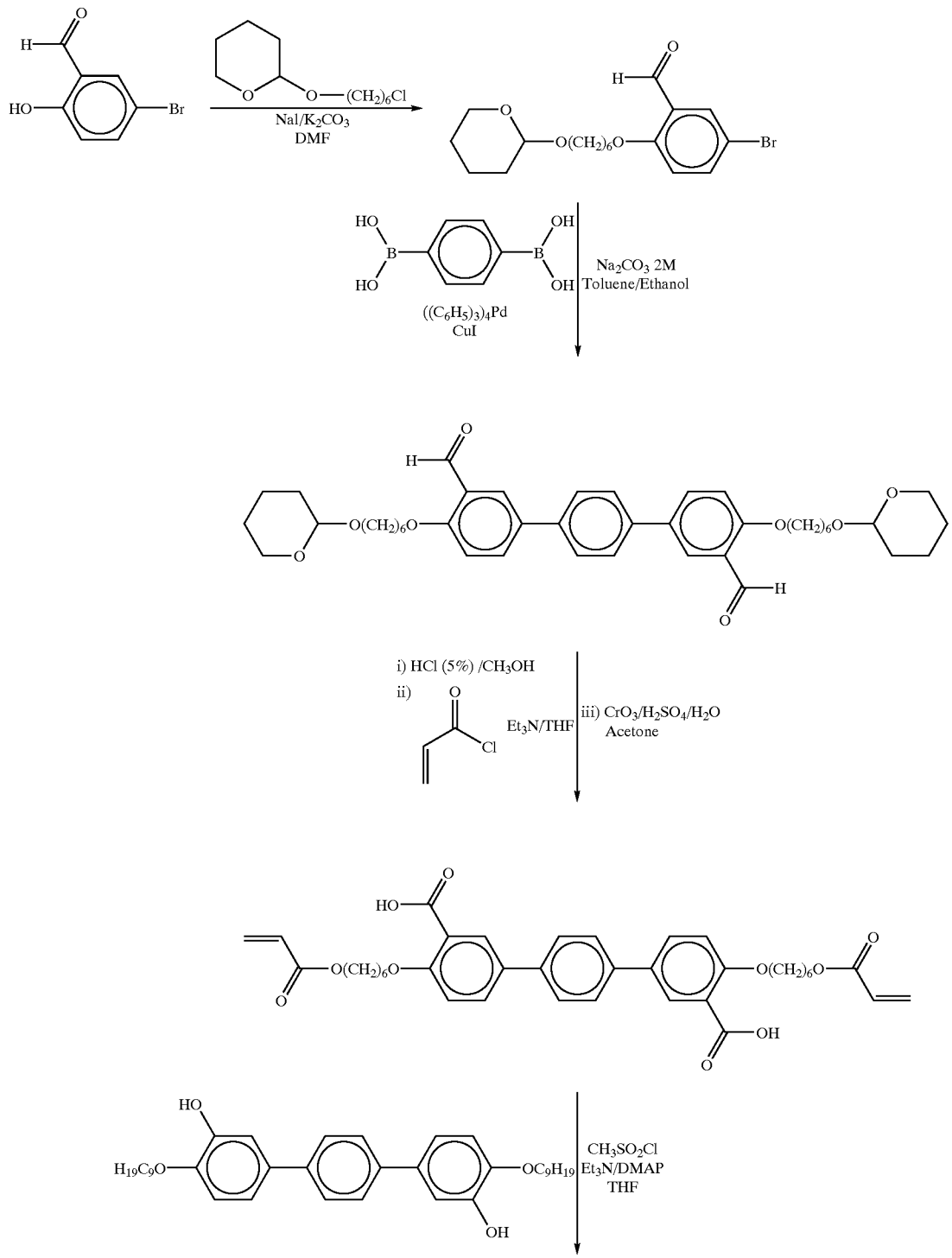

Scheme 7:
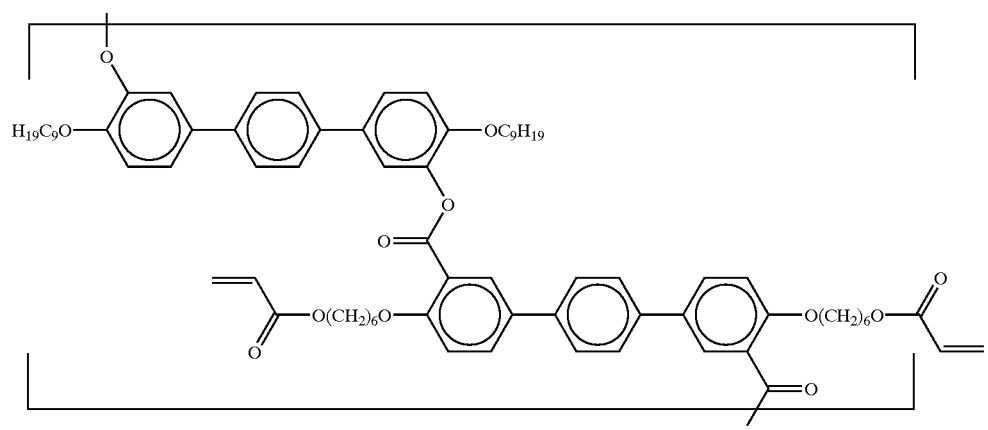
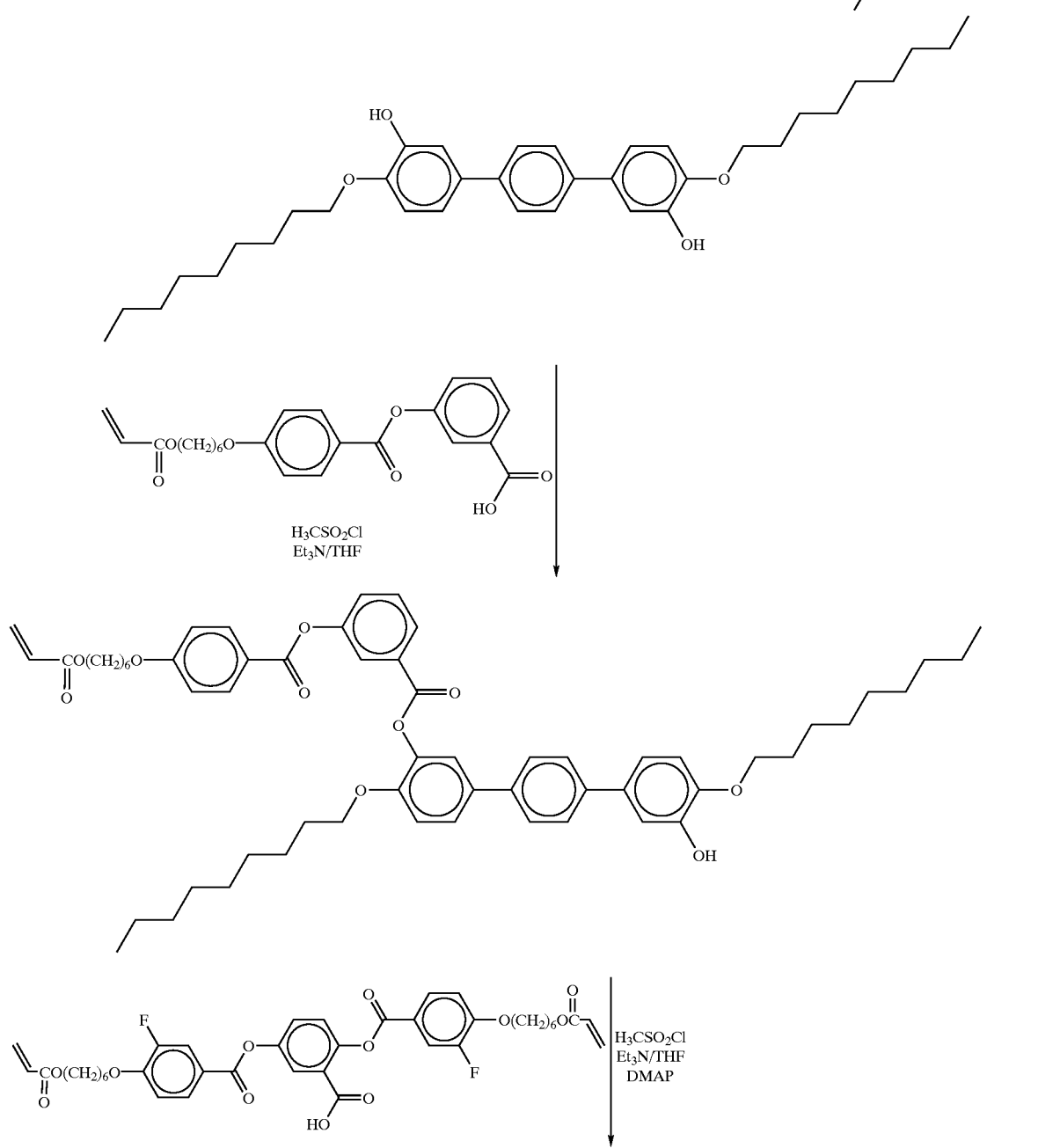

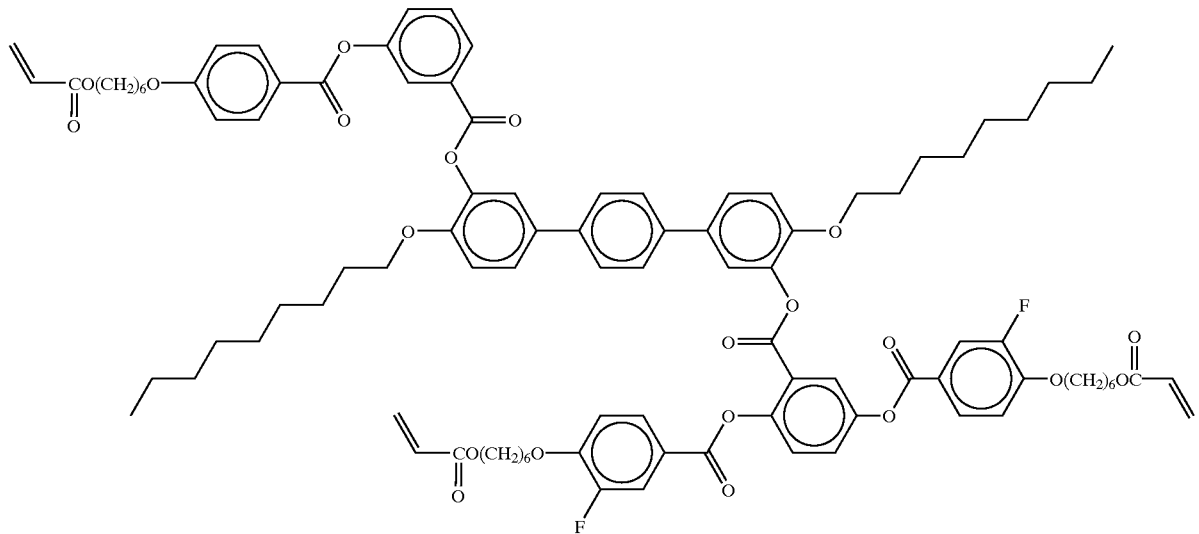
Based on the synthetic ways drawn in Schemes 1–7, typical examples representing "staircase" derivatives of formula I and shown in the following list of compounds may be prepared. This list is, however, to be understood only as illustrative without limiting the scope of the present invention:
(I.1)
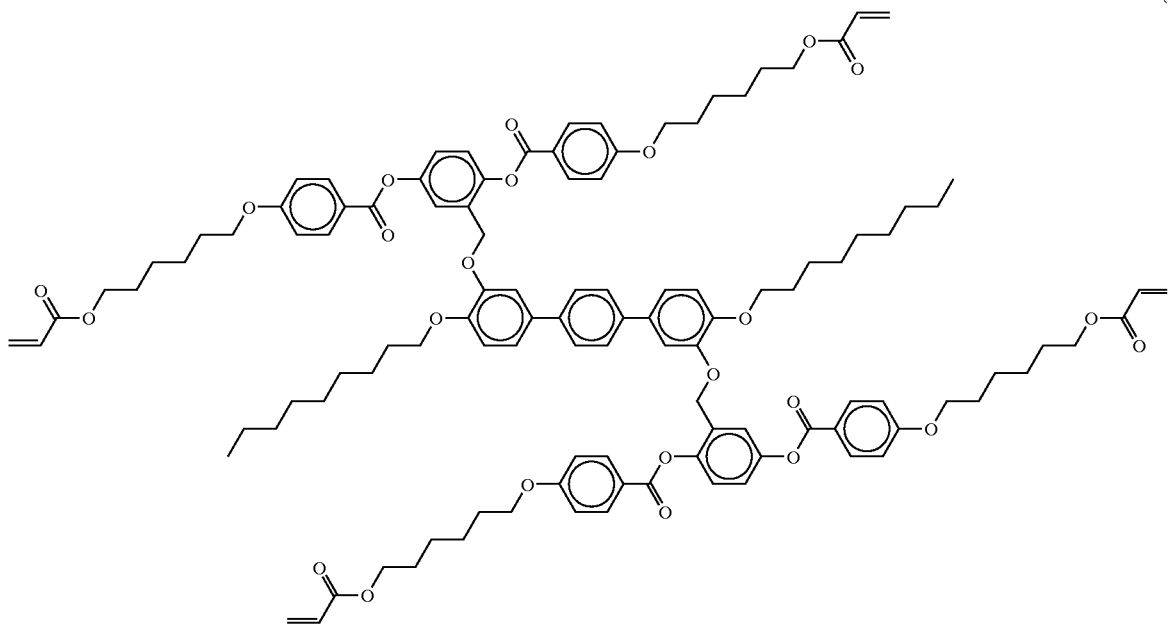

(I.2)
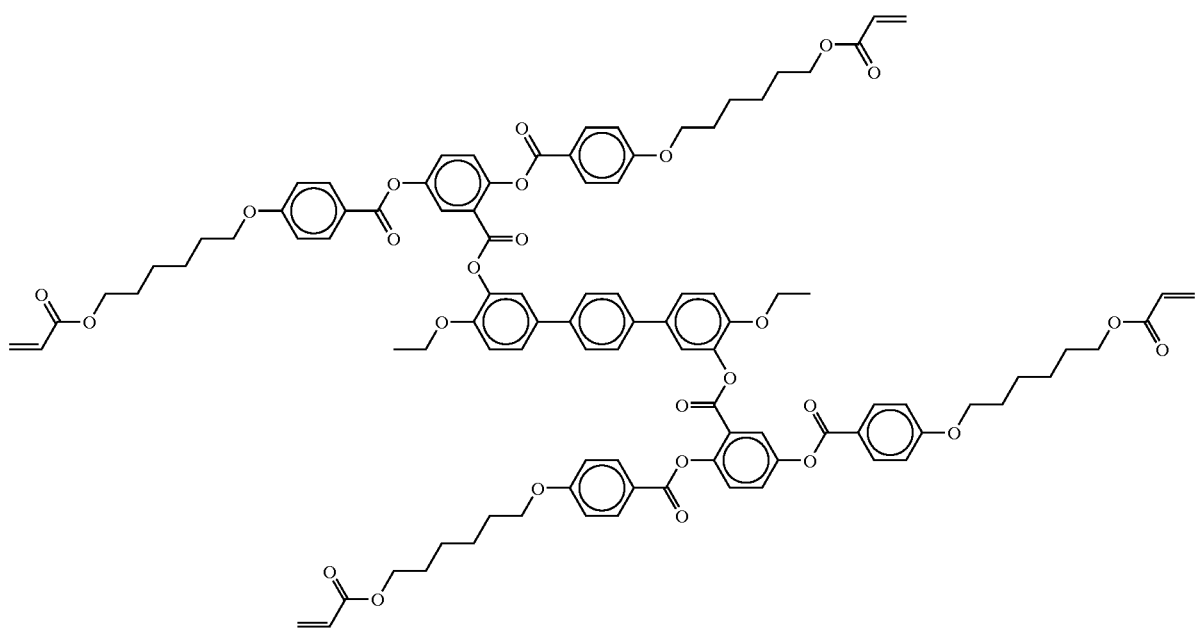
(I.3)
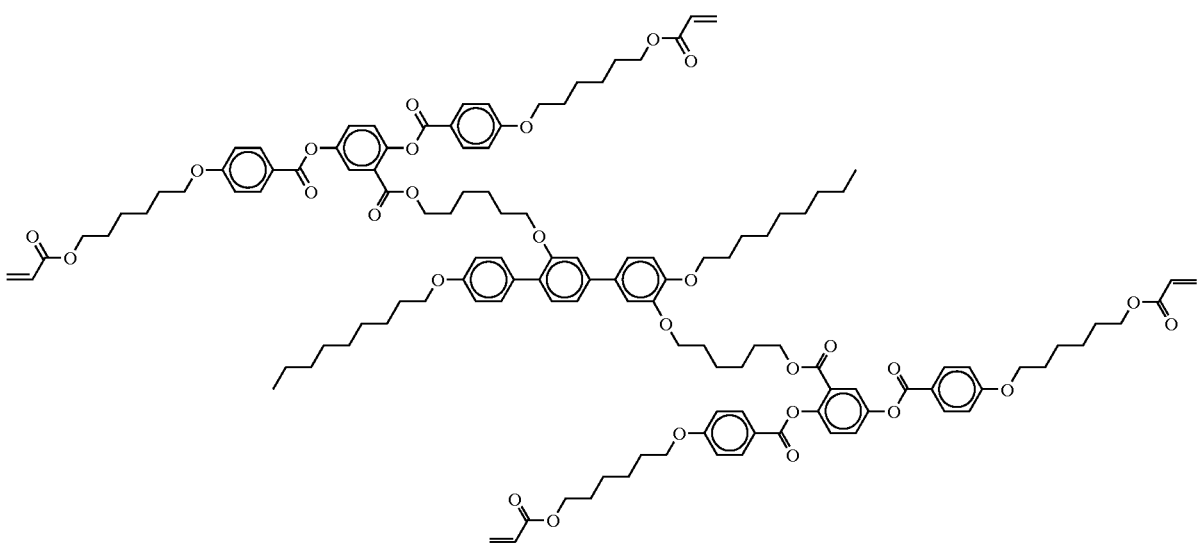

-continued
(I.4)
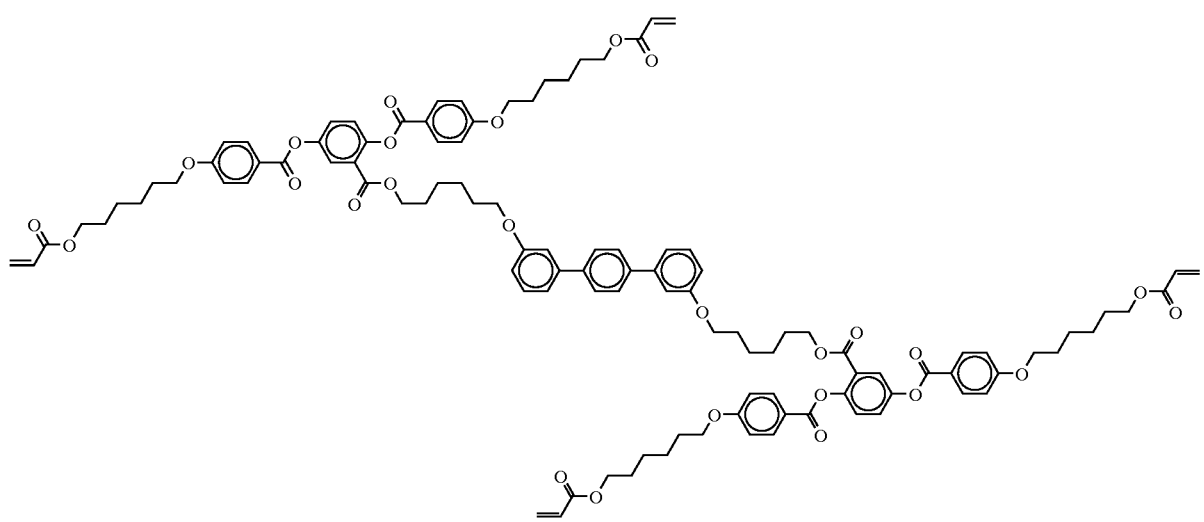
(I.5)
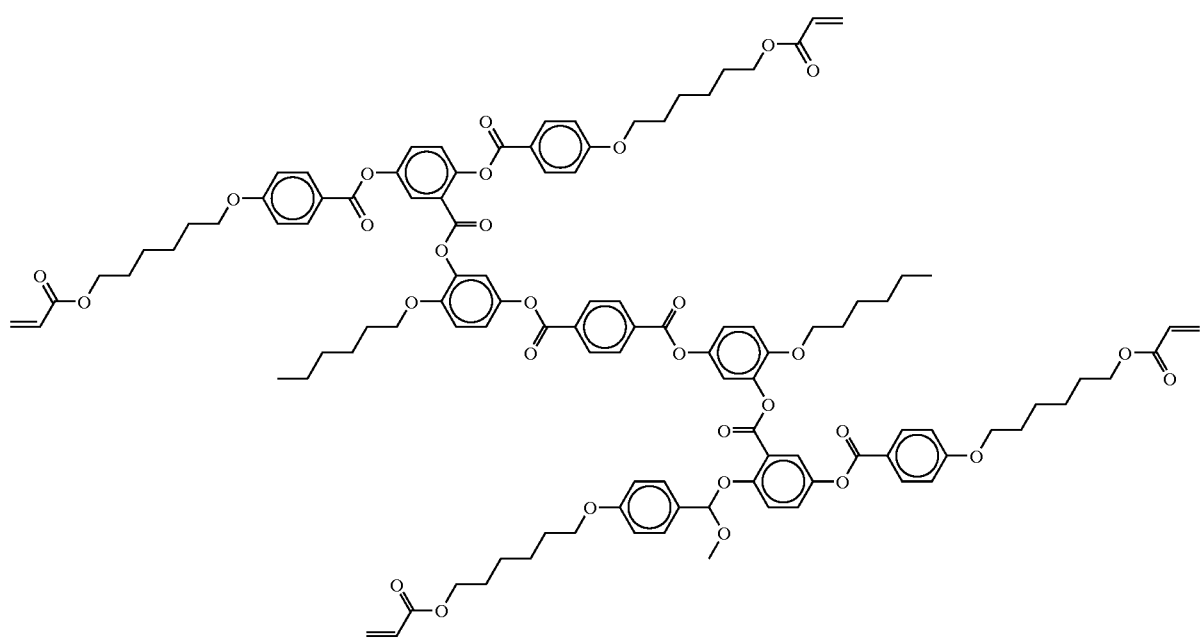

(I.6)
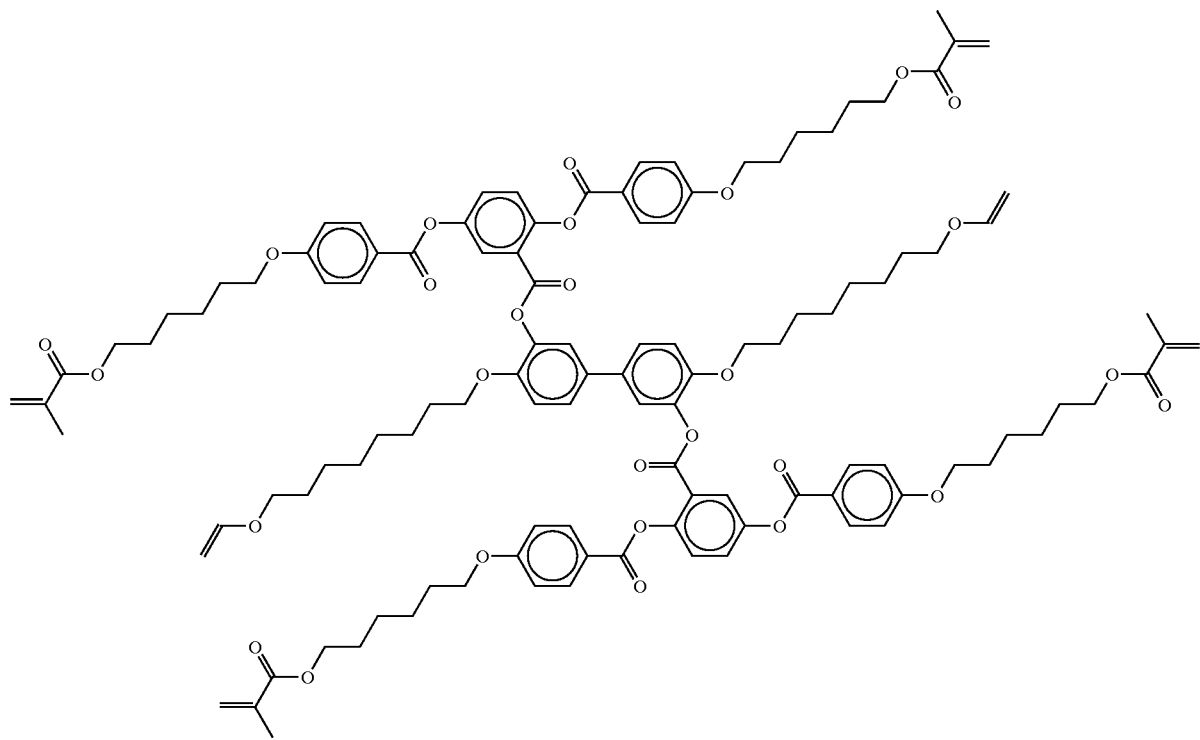
(I.7)
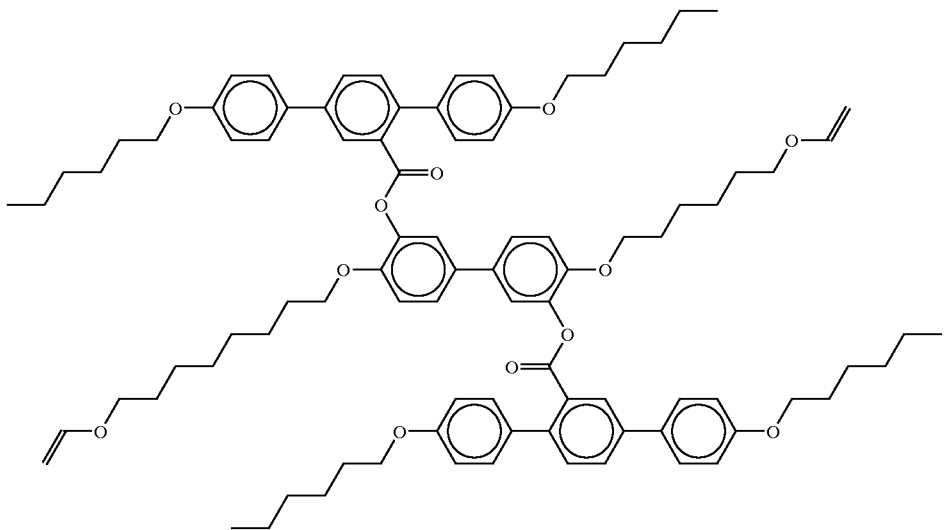

(I.8)
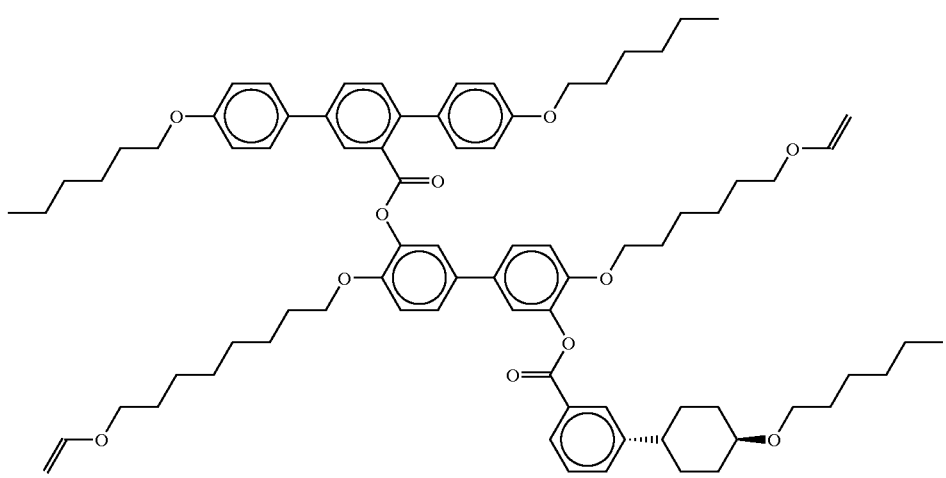
(I.9)
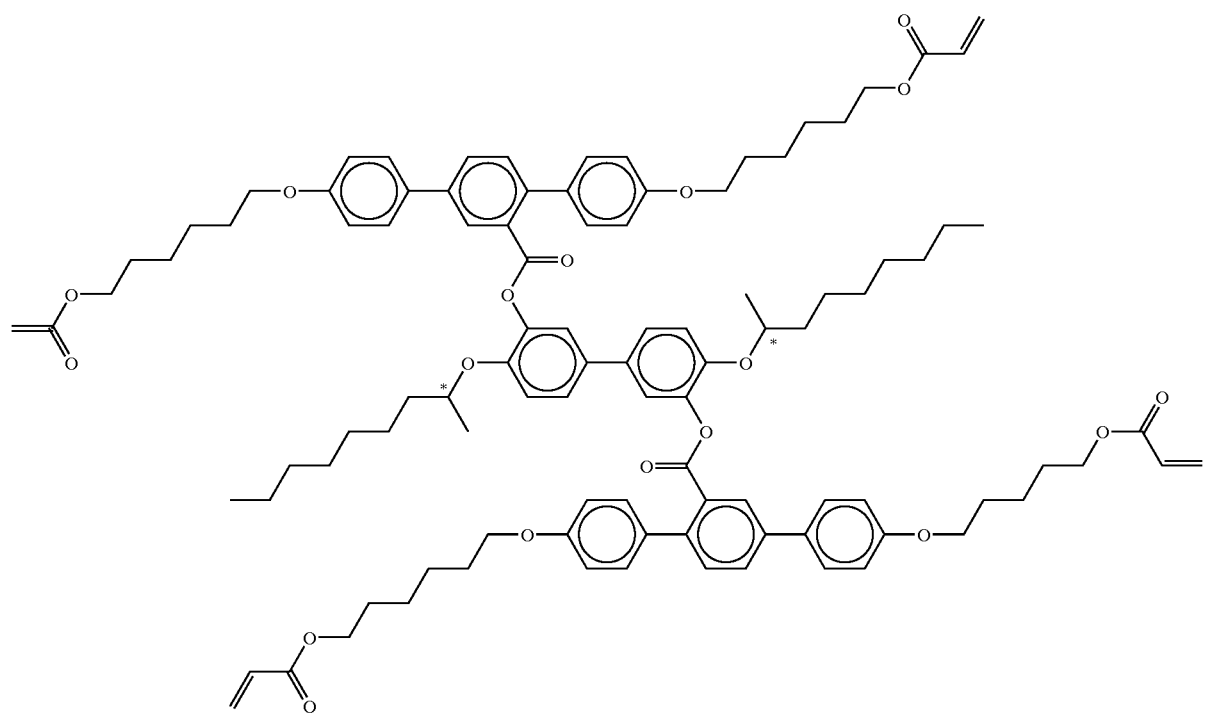

(I.10)
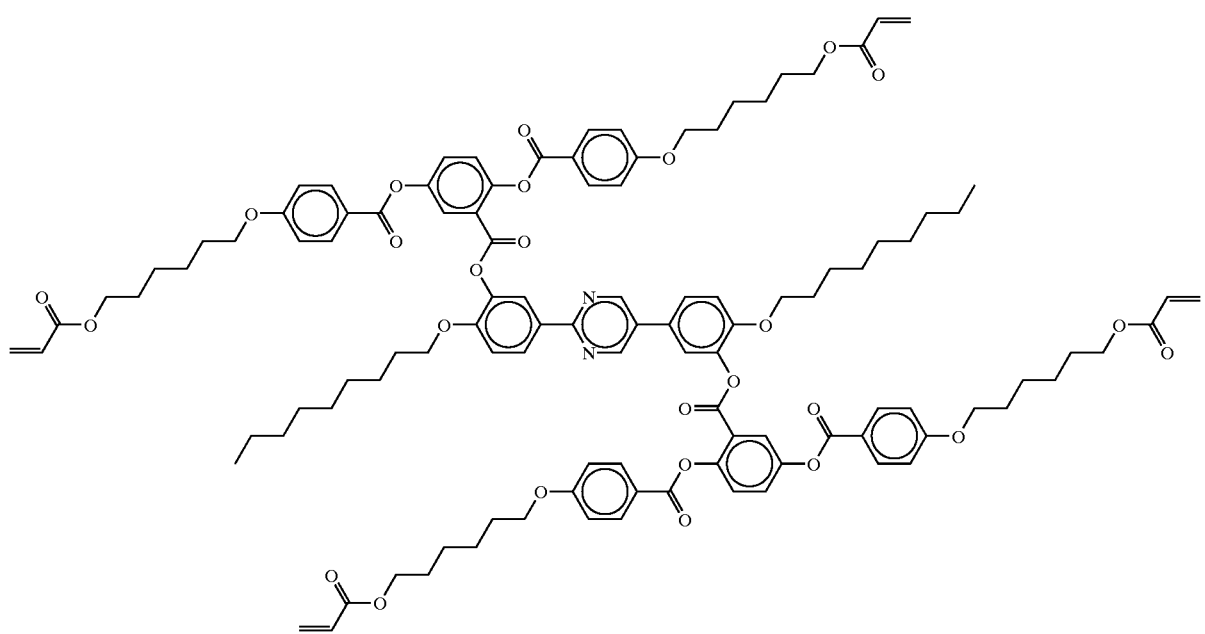
(I.11)
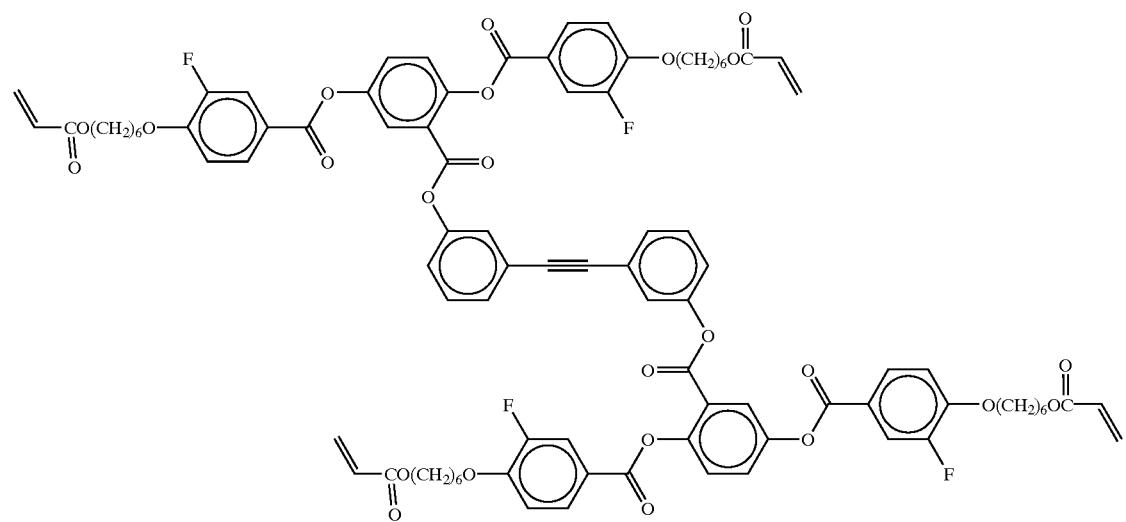

(I.12)
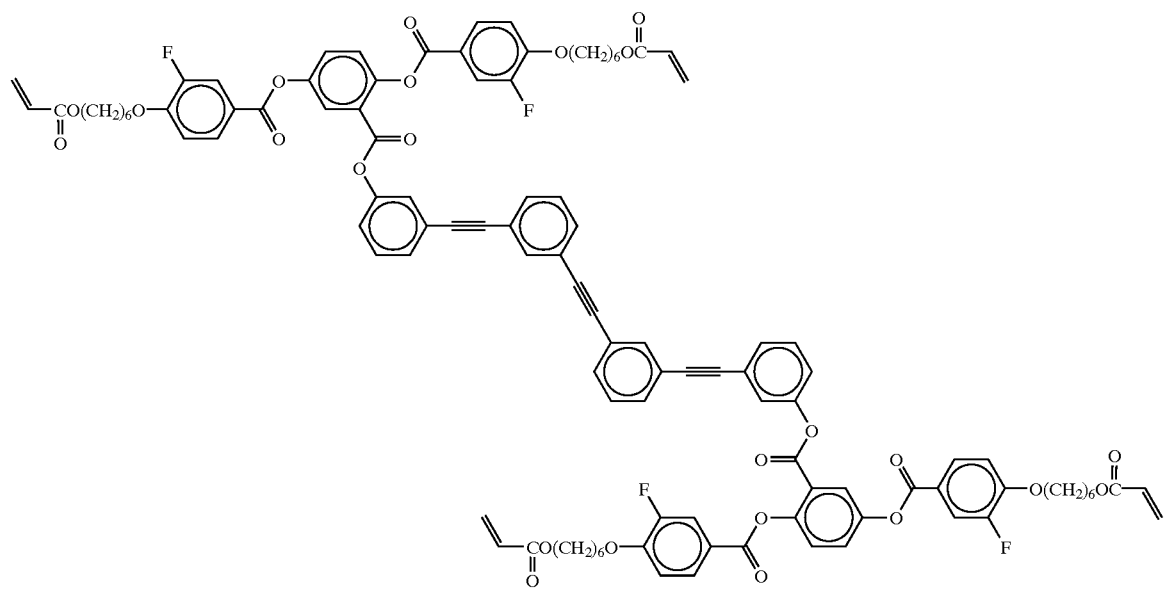
(I.13)
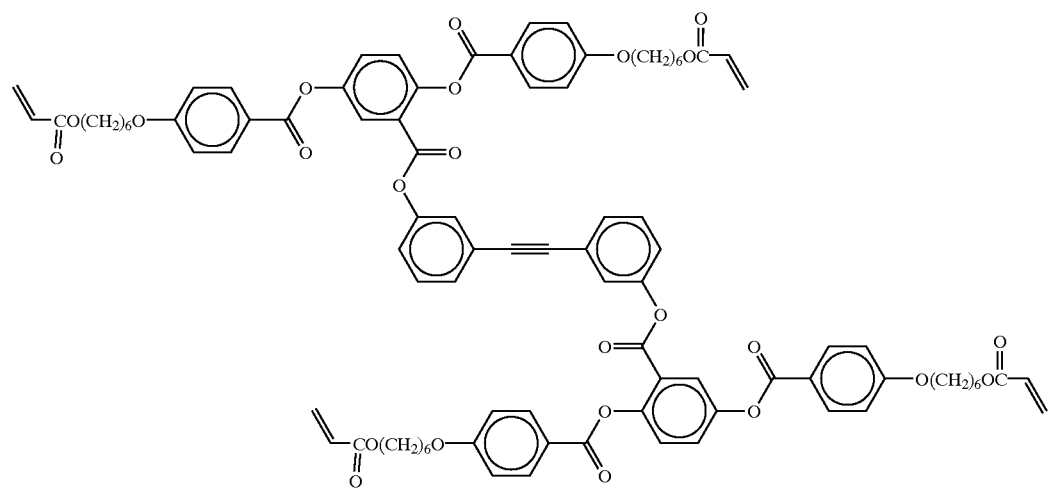
(I.14)
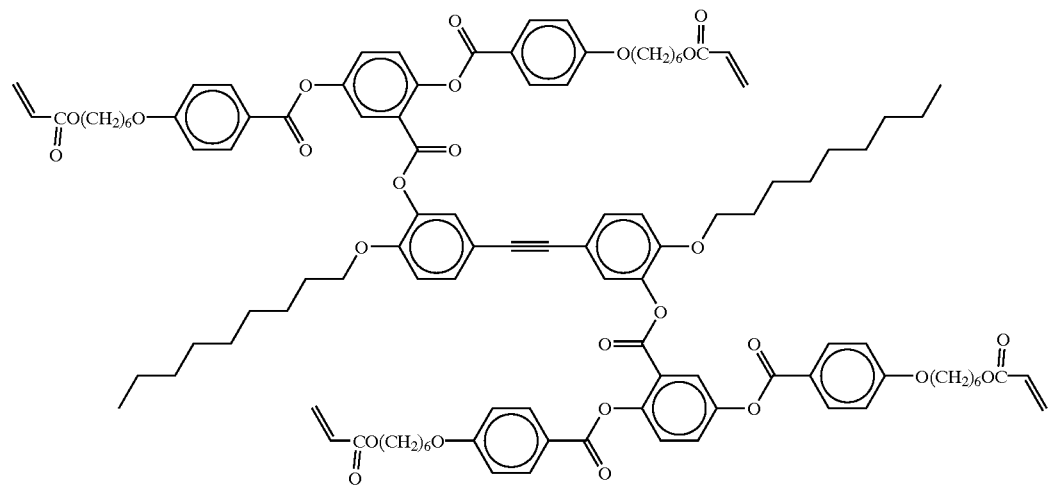

The "staircase" compounds of formula I disclosed in the foregoing and the following may be used alone or as a component of a liquid crystal mixture. Liquid crystalline LCPs. Another aspect of the invention therefore comprises a liquid crystalline material comprising a compound of formula (I). Preferably the liquid crystalline material comprises at least two components. The additional components must be miscible with the compound of formula (I) and may be selected from known mesogenic materials such as those reported in *Adv. Mater.* 5, 107 (1993), *Mol. Cryst. Liq. Cryst.* 307, 111 (1997), *J. Mat. Chem.* 5, 2047 (1995) or in patent applications U.S. Pat. Nos. 5,593,617; 5,567,349; GB-A-2 297 556; GB-A-2 299 333; DE-A-195 04 224; EP-A-0 606 940; EP-A-0 643 121 and EP-A-0 606 939, optionally selected from EP-A-0 606 940; EP-A-0 643 121 and EP-A-0 606 939.

The form of the liquid crystal material will depend upon the application in which it is to be used and may be present as a liquid crystalline mixture, (co)polymer, elastomer, polymer gel or polymer network. Polymer networks have been found to be of particular use and in a further preferred embodiment of the invention there is provided a polymer network comprising a compound of formula (I). Preferably the polymer network comprises at least two components, at least one of which is a "staircase" compound of formula (I).

The polymer network may be prepared by copolymerisation of a mesogenic mixture comprising:

i) at least one chiral or/and achiral mesogenic polymerisable compound;

ii) at least one "staircase" compound of formula I; and iii) an initiator.

The chiral or achiral mesogenic polymerisable compound may be a "staircase" compound of formula (I). Alternatively or in addition, the polymerisable compound may be selected from the known mesogenic materials referred to above. Preferably the chiral or achiral polymerisable compound includes the nematic phase in its thermotropic sequence.

The polymer network may optionally comprise further components. These include further polymerisable compounds, stabilisers and dyes. The additional polymerisable compounds preferably comprise a non-mesogenic compound having at least one polymerisable functional group, especially diacrylate compounds.

Any suitable stabiliser that prevents undesired spontaneous polymerisation, for example during storage of the mixture, may be used in the liquid crystalline mixture according to the invention. A broad range of these compounds is commercially available. Typical examples include 4-ethoxyphenol or 2,6-di-tert-butyl-4-methylphenol (BHT).

If colour filters are required, dyes may be added to the mixture. In a preferred embodiment of the invention the LC mixture contains no dye.

The chiral or achiral polymerisable mesogenic compound may be present in an amount comprising 0.01 to 99% by weight of the liquid crystalline polymer network mixture, preferably 50 to 95% by weight.

The "staircase" compound of formula (I) may be present in an amount from 0.1 to 100% by weight of the liquid crystalline network, preferably from 1 to 50% by weight.

The initiator is preferably a photoinitiator and may be a radical or cationic initiator that is present in an amount comprising 0.1 to 5% by weight of the polymer mixture, preferably from 0.2 to 2% by weight.

When the mixture further comprises a stabiliser, this is generally present in an amount comprising 0.01 to 5% by weight of the liquid crystalline mixture, preferably from 0.1 to 1% by weight.

These polymerisable liquid crystalline mixtures may be formed into liquid crystalline polymer (LCP) films and a fifth aspect of the invention provides a LCP film comprising a compound of formula (I). LCP films may be readily prepared by UV polymerisation of a LC mixture according to the invention; a film comprising the LC mixture is formed on a substrate and polymerised using UV light to give a cross-linked liquid crystal polymer (LCP) film. The film is both light and temperature stable and can be used in the manufacture of devices such as waveguides, optical gratings, filters, retarders, piezoelectric cells or thin films exhibiting non-linear optical properties.

Different methods can be used for the formation of the sought LCP network, starting from the polymerisable liquid crystalline mixture manufactured as described above. Transparent substrates such as coated ITO (indium tin oxide), glass or plastic substrates, may be used. Preferred substrates include glass or plastic, especially those including a layer of rubbed polyimide or polyamide or a layer of photo-oriented photopolymer (LPP). Said layers are used to facilitate uniform orientation of the liquid crystalline mixture.

In the preparation of LCP films, it is particularly important to prevent the formation of defects or inhomogenities. This can be achieved by forming the polymerisable liquid crystalline mixture into a thin film; and placing the mixture between two of the aforementioned substrates which are then sheared over a small distance until a planar order was obtained; or capillary filling the polymerisable liquid crystalline mixture between two of the said substrates; prior to curing, for example by UV light, preferably in the presence of a photoinitiator, such as IRGACURE™.

A further aspect of the invention provides an optical or electro-optical component containing a liquid crystalline polymer film comprising a compound of formula (I). The optical or electro-optical component may be a waveguide, an optical gratings, a filter, a retarder, a piezoelectric cell or a non-linear optical cell or film.

The invention will now be described with reference to the following examples. Variations on these falling within the scope of the invention will be apparent to a person skilled in the art.

In the following Examples the thermotropic phases are abbreviated as follows:

K crystalline
D discotic
S smectic
N nematic
N* chiral nematic (cholesteric)
I isotropic

EXAMPLE 1

2,5-Bis-[4-(6-acryloyloxyhexyloxy)benzoyloxy]
benzoic acid 5'-[2,5-bis-[4-(6-acryloyloxyhexyloxy)
benzoyloxy]benzoyloxy]-4,4"-dipentyl[1,1';4',1"]
terphenyl-2'-yl ester.

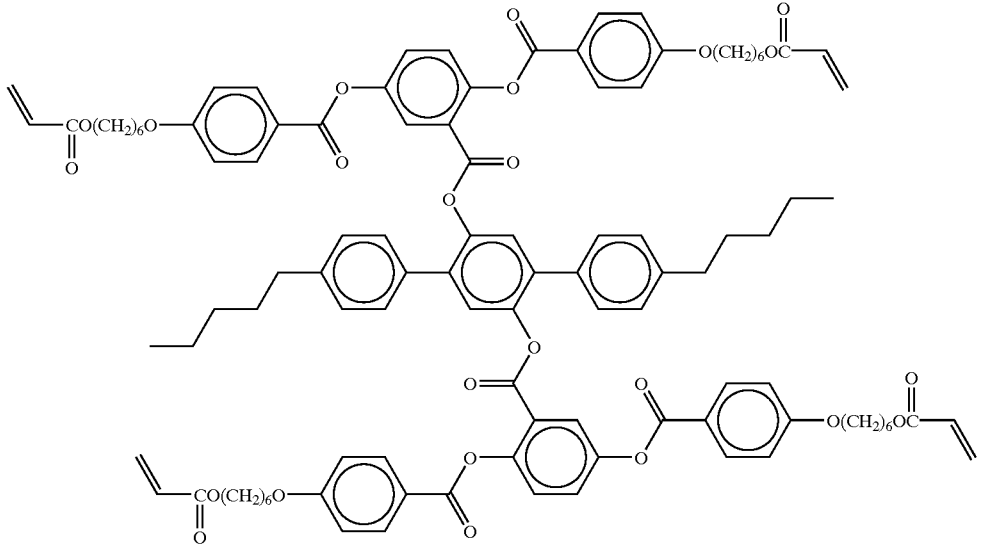

1) 2',5'-Dimethoxy-4,4"-dipentyl[1,1';4',1"]terphenyl

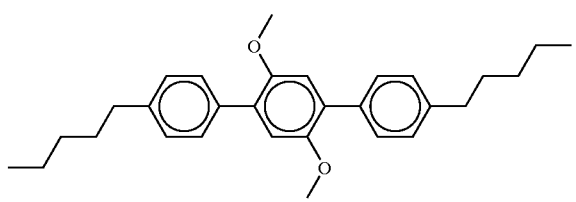

To a well degassed mixture of 4-pentylbenzeneboronic acid (3.84 g), 1,4-dibromo-2,5-dimethoxybenzene (2.95 g), Na$_2$CO$_3$ 2M (40 ml), ethanol (15 ml) and toluene (25 ml), tetrakis(triphenylphosphine)palladium(0) (0.62 g) is added and the obtained mixture is maintained under argon atmosphere and vigorously stirred at reflux for two hours. The cooled reaction mixture is extracted with ether (3×80 ml) and the combined ether extracts are washed with saturated NaCl solution (120 ml) dried over magnesium sulphate and evaporated to dryness. The obtained dark residue is filtered through a short silica gel column to afford 2',5'-dimethoxy-4,4"-dipentyl[1,1';4',1"]terphenyl as white crystalline material.

Yield: 3.9 g.

2) 4,4"-Dipentyl[1,1';4',1"]terphenyl-2',5'-diol

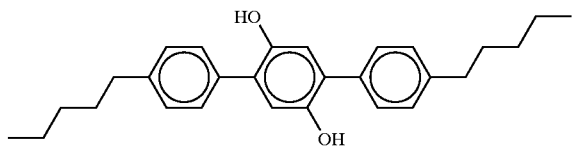

A solution of 2',5'-dimethoxy-4,4"-dipentyl[1,1';4',1"]terphenyl (2.15 g) in dichloromethane (40 ml) is cooled to −76° C. and treated with a dropwise addition of 1 M solution of boron tribromide in CH$_2$Cl$_2$ (12 ml). After complete addition the reaction mixture is allowed to reach room temperature and stirring is continued for 6 hours. The reaction mixture is then carefully poured into ice-water (100 g) and stirred for further 20 min. The obtained mixture is then saturated with NaCl and extracted with diethyl ether (3×150 ml). The combined organic extracts are washed with saturated NaCl solution (150 ml), dried over magnesium sulphate and evaporated under reduced pressure to afford 4,4"-dipentyl[1,1';4',1"]terphenyl-2',5'-diol as white crystalline material.

Yield 1.8 g.

3) 2,5-Bis-[4-(6-acryloyloxyhexyloxy)benzoyloxy]benzoic acid 5'-[2,5-bis-[4-(6-acryloyloxyhexyloxy)benzoyloxy]benzoyloxy]-4,4"-dipentyl[1,1';4',1"]terphenyl-2'-yl ester.

To a solution of 4,4"-dipentyl[1,1';4',1"]terphenyl-2',5'-diol (0.11 g), 2,5-di-[4-(6-acryloyloxyhexyloxy)benzoyloxy]benzoic acid (0.42 g) and 4-dimethylaminopyridine (DMAP) (7 mg) in dichloromethane (8 ml), cooled at 0° C., a solution of N,N'-dicyclohexylcarbodiimide (DCC) (0.12 g) in dichloromethane (2 ml) is added dropwise. After complete addition, the reaction mixture is stirred at room temperature for 6 h then evaporated under reduced pressure. The obtained crude white residue is chromatographed on silica (dichloromethane/diethyl ether:19/1) to afford pure 2,5-bis-[4-(6-acryloyloxyhexyloxy)benzoyloxy]benzoic acid 5'-[2,5-bis[4-(6-acryloyloxyhexyloxy)benzoyloxy]benzoyloxy]-4,4"-dipentyl[1,1';4',1"]terphenyl-2'-yl ester as white crystalline material.

Yield: 0.32 g.

This compound has the following thermotropic sequence: K 172° C. I.

EXAMPLE 2

2,5-Bis-[4-(6-acryloyloxyhexyloxy)benzoyloxy]
benzoic acid 3-[2,5-bis-[4-(6-acryloyloxyhexyloxy)
benzoyloxy]benzoyloxy]-4,4''-bisnonyloxy[1,1';4',
1''] terphenyl-3''-yl ester

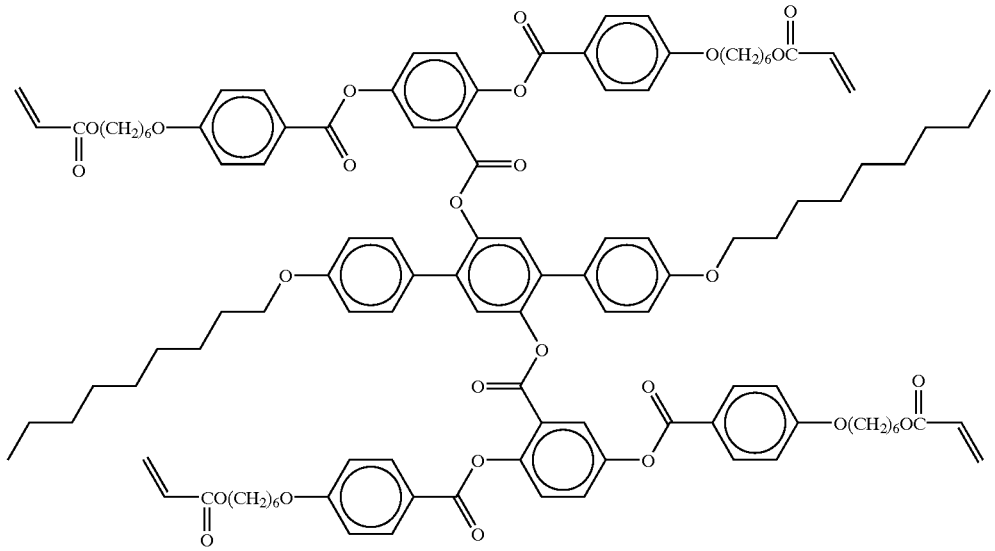

1) 4,4'-Dinonyloxy[1,1';4',1'']terphenyl-3,3''-dicarbaldehyde

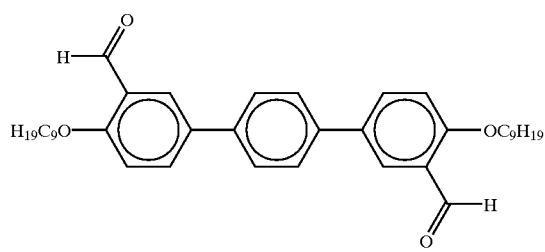

To a well degassed mixture of 1,4-benzenediboronic acid (1.4 g), 5-bromo-2-nonyloxybenzaldehyde (5.50 g), Na$_2$CO$_3$ 2M (40 ml), ethanol (15 ml) and toluene (40 ml), tetrakis(triphenylphosphine)palladium(0) (0.62 g) and CuI (5 mg) are added. The obtained mixture is maintained under argon atmosphere and vigorously stirred at reflux for 12 h. After cooling the organic layer is separated and the aqueous phase is extracted with 2×60 ml of ether and the combined organic extracts are dried over magnesium sulphate and evaporated to dryness. The obtained black residue is chromatographed on silica using CH$_2$Cl$_2$/hexane: 3/1 as eluant. The obtained yellow crystalline material is dissolved in minimum of CH$_2$Cl$_2$ (30 ml) and poured into 200 ml of acetone. The obtained solution is half-concentrated and cooled at 0° C. for 2 h. The pure 4,4'-dinonyloxy[1,1';4',1'']terphenyl-3,3''-dicarbaldehyde crystallises as white powder.

Yield: 3.8 g.

2) 4,4''-Dinonyloxy[1,1';4',1'']terphenyl-3,3''-diol

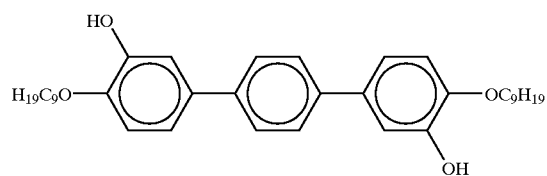

A solution of 4,4''-dinonyloxy[1,1';4',1'']terphenyl-3,3''-dicarbaldehyde (3.42 g) in CH$_2$Cl$_2$ (120 ml) is cooled at 0° C. and treated with two crops addition of m-chloroperbenzoic acid (3.83 g). The mixture is stirred at room temperature for 3 h. It is then quenched with saturated solution of NaHCO$_3$ (50 ml) and extracted twice with ether (2×200 ml). The combined organic extracts are further washed with saturated solution of NaHCO$_3$ (100 ml), with saturated solution of NaCl, dried over magnesium sulphate and evaporated to afford a yellow crystalline residue. This residue is dissolved in ethanol/dichloromethane: 50 ml/30 ml and treated with 75 ml of 1.5 M KOH at 55° C. for 20 min. The resulting mixture is then concentrated and extracted with ether (3×150 ml). The ether extracts are washed with sat. NaCl (2×200 ml), dried over magnesium sulphate and evaporated to dryness. This affords the dihydroxy compound as yellow crystalline material which is purified by recrystallisation in ethanol to give 4,4''-dinonyloxy[1,1';4',1'']terphenyl-3,3''-diol as a slightly yellow crystalline material.

Yield: 3.1 g.

3) 2,5-Bis-[4-(6-acryloyloxyhexyloxy)benzoyloxy]benzoic acid 3-[2,5-bis-[4-(6-acryloyloxyhexyloxy)benzoyloxy]benzoyloxy]4,4''-bisnonyloxyl[1,1';4',1'']terphenyl-3''-yl ester A solution of mesyl chloride (0.73 g) in 10 ml of dry THF is dropwise added to a solution of 2',5'-bis-[2,5-di-(4-

(6acryloyloxyhexyloxy)benzoyloxy)]benzoic acid (4.50 g) and triethylamine (3.6 ml) in 50 ml of dry THF, cooled at −25° C. and maintained and under argon atmosphere. After complete addition (15 min), the reaction mixture is further stirred for 120 min at −25° C. then treated with a solution of 4,4"-dinonyloxy[1,1';4',1"]terphenyl-3,3"-diol in 60 ml of dry THF containing 78 mg of DMAP and the reaction mixture is further stirred at −25° C. for 2 h. The temperature is then allowed to reach room temperature and stirring is continued overnight. The reaction mixture is poured into 120 ml of water, extracted with 2×200 ml of ether and 120 ml of dichloromethane. The combined organic extracts are washed with HCl 3N (200 ml) then with a half saturated NaCl solution (2×100 ml), dried over MgSO$_4$ and evaporated to dryness to afford a slightly yellow pasty material. This is dissolved in 25 ml of THF and reprecipitated from 300 of methanol, then flash chromatographed over a short silica column.

Pure 2,5-bis-[4-(6acryloyloxyhexyloxy)benzoyloxy]benzoic acid 3-[2,5-bis-[4-(6-acryloyloxyhexyloxy)benzoyloxy]benzoyloxy]4,4"-bisnonyloxy[1,1';4',1"]terphenyl-3"-yl ester is obtained as a white crystalline material.

Yield: 4.7 g.

This compound has the following thermotropic sequence: K 105.5° C. N 122.6° C. I.

When the sample is quickly cooled from the isotropic state, the nematic mesophase still occurs at room temperature for 2 hours before the crystallisation.

EXAMPLE 3

2-[4-(6-acryloyloxyhexyloxy)benzoyloxy]-5-(trans-4-pentylcyclohexanecarbonyloxy)benzoic acid 3-[2-[4-(6-acryloyloxyhexyloxy)benzoyloxy]-5-trans-4-pentylcyclohexanecarbonyloxy)]benzoyloxy]-4,4"-bisnonyloxy[1';4',1"]terphenyl-3"-yl ester

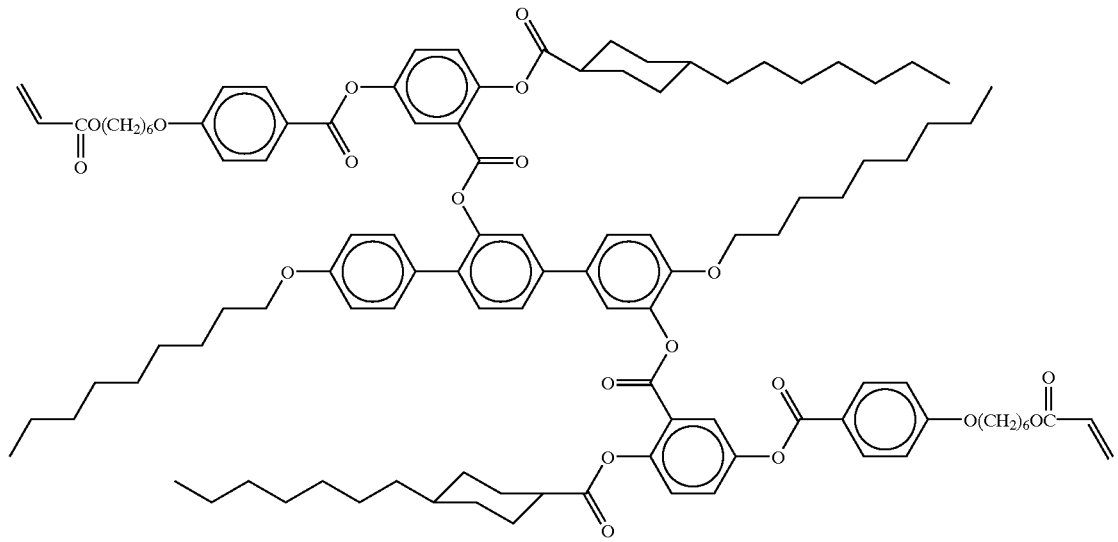

1) 2-[4-(6-Acryloyloxyhexyloxy)benzoyloxy]-5-(4-trans-pentylcyclohexanecarbonyloxy)benzaldehyde

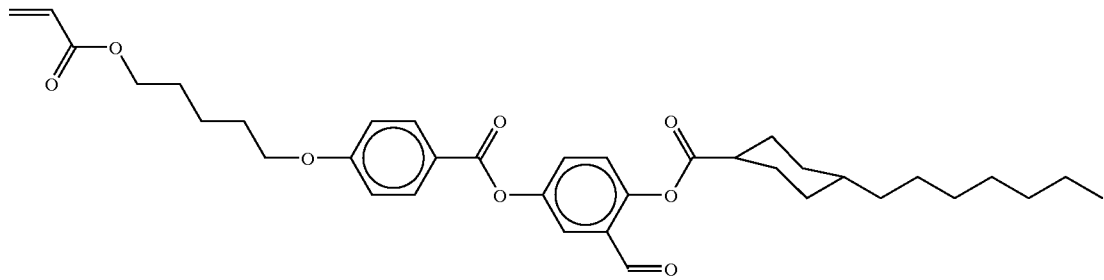

A solution of mesyl chloride (1.14 g) in 10 ml of dry THF is dropwise added to a cooled (−40 to −25° C.) solution of 4-(6-acryloyloxyhexyloxy)benzoic acid (2.78 g) and triethylamine (6 ml) in 40 ml of dry THF and under argon. After complete addition (15 min), the reaction mixture was further stirred for 60 min at −25° C. then treated with a solution of 2,5-dihydroxybenzaldehyde (1.38 g) in 10 ml of dry THF and the reaction mixture is further stirred at −25° C. for 2 h.

This mixture was then treated with a suspension of triethyl-(trans-4-pentylcyclohexynecarbonyl)ammonium; chloride (prepared from trans-4-pentylcyclohexanecarboxylic acid (2.26 g), triethylamine (6 ml) and mesyl chloride (1.14 g) in THF(35 ml)) in dry THF (35 ml), followed by one-crop addition of DMAP (0.24 g). Stirring is continued for 3 h at −25° C. and for 30 min at room temperature. The reaction mixture is then poured into 80 ml of saturated NaHCO$_3$, extracted with 2×100 ml of ether. The combined organic extracts are washed with HCl 3N (100 ml) then with half saturated NaCl solution (2×100 ml), dried over MgSO$_4$, filtered and evaporated to dryness to afford a slightly yellow pasty material. This is flash chromatographed over a short silica-gel column (CH$_2$Cl$_2$). The obtained white residue (2.3 g) was dissolved in CH$_2$Cl$_2$ (5 ml) then reprecipitated from ethanol (50 ml). This affords pure 2-[4-(6-acryloyloxyhexyloxy)benzoyloxy]5-(4-trans-pentylcyclohexanecarbonyloxy)benzaldehyde as white crystalline material.

Yield 1.3 g.

2) 2-[4-(6-Acryloyloxyhexyloxy)benzoyloxy]-5-(4-trans-pentylcyclohexanecarbonyloxy)benzoic acid

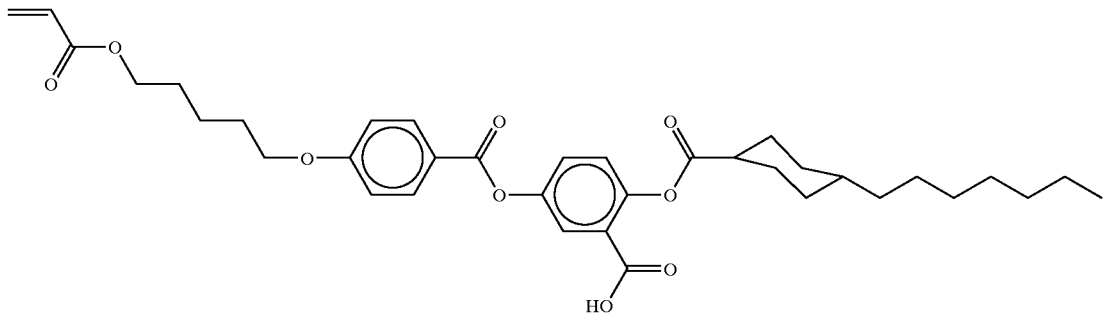

Jones oxidant (CrO$_3$/H$_2$SO$_4$/H$_2$O) (8 ml) is added dropwise to a ice-cooled solution of 2-[4-(6-acryloyloxyhexyloxy)benzoyloxy]-5-(4-trans-pentylcyclohexanecarbonyloxy)benzaldehyde (1.21 g) in acetone/dichloromethane (40 ml/20 ml). After complete addition (10 min), stirring is continued at room temperature overnight. The green-orange mixture is then filtered off and the green precipitate is washed with 150 ml of ether. The combined organic solutions are then washed with water until the orange coloration is removed (6×100 ml). The obtained colourless organic solution is washed with saturated NaCl solution (2×80 ml), dried over MgSO4, filtered and evaporated to dryness. 2-[4-(6-acryloyloxyhexyloxy) benzoyloxy]-5-(4-trans-pentylcyclohexanecarbonyloxy) benzoic acid as white crystalline material.

Yield 1.18 g.

3) 2-[4-(6-acryloyloxyhexyloxy)benzoyloxy]-5-(trans-4-pentylcyclohexanecarbonyloxy)benzoic acid 3-[2-[4-(6-acryloyloxyhexyloxy)benzoyloxy]-5-(trans-4-pentylcyclohexanecarbonyloxy)]benzoyloxy]-4,4"-bisnonyloxy[1,1'4',1"]terphenyl-3"-yl ester.

Following the procedure described in Example 2, the reaction was performed with 1.1 g of 2-[4-(6-Acryloyloxyhexyloxy)benzoyloxy]-5-(4-trans-pentylcyclohexanecarbonyloxy)benzoic acid , 0.37 g of 4,4"-dinonyloxy[1,1';4',1"]terphenyl-3,3"-diol, 0.02 g of DMAP, 2 ml of triethylamine and 0.2 g of mesyl chloride affording the desired compound as white crystalline material.

Yield 0.81 g.

This compound presents the nematic mesophase as a single liquid-crystalline phase at a temperature above 90° C. and thermally polymerises at this temperature.

EXAMPLE 4

2,5-Bis-[4-(6-acryloyloxyhexyloxy)benzoyloxy] benzoic acid 3-[3-[2,5-bis-[4-(6-acryloyloxyhexyloxy)benzoyloxy]benzoyloxy] phenylethynyl]phenyl ester 1) 3-(3-Ethynylphenoxy)tetrahydropyran

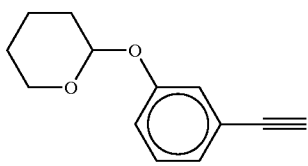

To a well degassed solution of 3-(3-bromophenoxy) tetrahydropyran (5.14 g), triphenylphosphine (204 mg), copper(I) iodide (38 mg) and bis(triphenylphosphine) palladium(II) dichloride (3.93 g) in triethylamine (40 ml), maintained under argon atmosphere, trimethylsilylacetylene is added and the mixture is stirred at 85° C. for 3 h. The precipitated ammonium salts was removed by filtration and the filtrate was evaporated to dryness. This affords a yellowish oil which is dissolved in 30 ml of THF containing 3 ml of water, then cooled at 0° C. and treated by dropwise addition of 5 ml of tetrabutylammonium fluoride (1M in THF). After stirring for 30 min the reaction was complete and the obtained brownish solution was filtered over a short silica-gel column and concentrated to yield a brownish residue, which was chromatographed on silica-gel column affording 3-(3-ethynylphenoxy)tetrahydropyran as yellowish crystals.

Yield 3.8 g.

2) 1,2-Bis-(3-hydroxyphenyl)ethyne

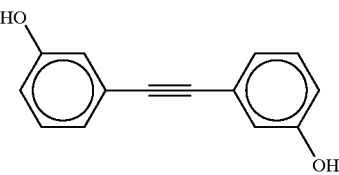

Following the above procedure, the reaction was performed with 3-(3-bromophenoxy)tetrahydropyran (2.57 g), 3-(3 -ethynylphenoxy)tetrahydropyran (2.02 g), triphenylphosphine (105 mg), copper(I) iodide (19 mg) and bis(triphenylphosphine)palladium(II) dichloride (70 mg) in triethylamine (40 ml). The crude dark residue obtained after filtration over silica-gel column is dissolved in a mixture of dichloromethane (10 ml) and methanol (40 ml), then treated with 150 mg pyridinium p-toluene sulphonate at 60° C. for 2 h. The transparent reaction solution was then diluted with 100 ml of ether and washed twice with 40 ml of water then with 50 ml of saturated NaCl solution, dried over MgSO4 and evaporated to dryness to afford 1,2-bis-(3-hydroxyphenyl)ethyne as yellowish solid.

Yield 1.66 g.

3) 2,5-Bis-[4-(6-acryloyloxyhexyloxy)benzoyloxy]benzoic acid 3-[3-[2,5-bis-[4-(6-acryloyloxyhexyloxy)benzoyloxy]benzoyloxy]phenylethynyl]phenyl ester Following the procedure described in Example 2, the reaction was performed with 1.4 g of 2',5'-bis-[2,5-di-(4-(6acryloyloxyhexyloxy)benzoyloxy)]benzoic acid, 0.14 g of 1,2-bis-(3-hydroxyphenyl)ethyne, 0.012 g of DMAP, 1.4 ml of triethylamine and 0.23 g of mesyl chloride affording the desired compound as white pasty material.

Yield 0.64 g.

This compound present the following thermotropic sequence:

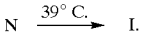

EXAMPLE 5

A mixture is formulated consisting of:

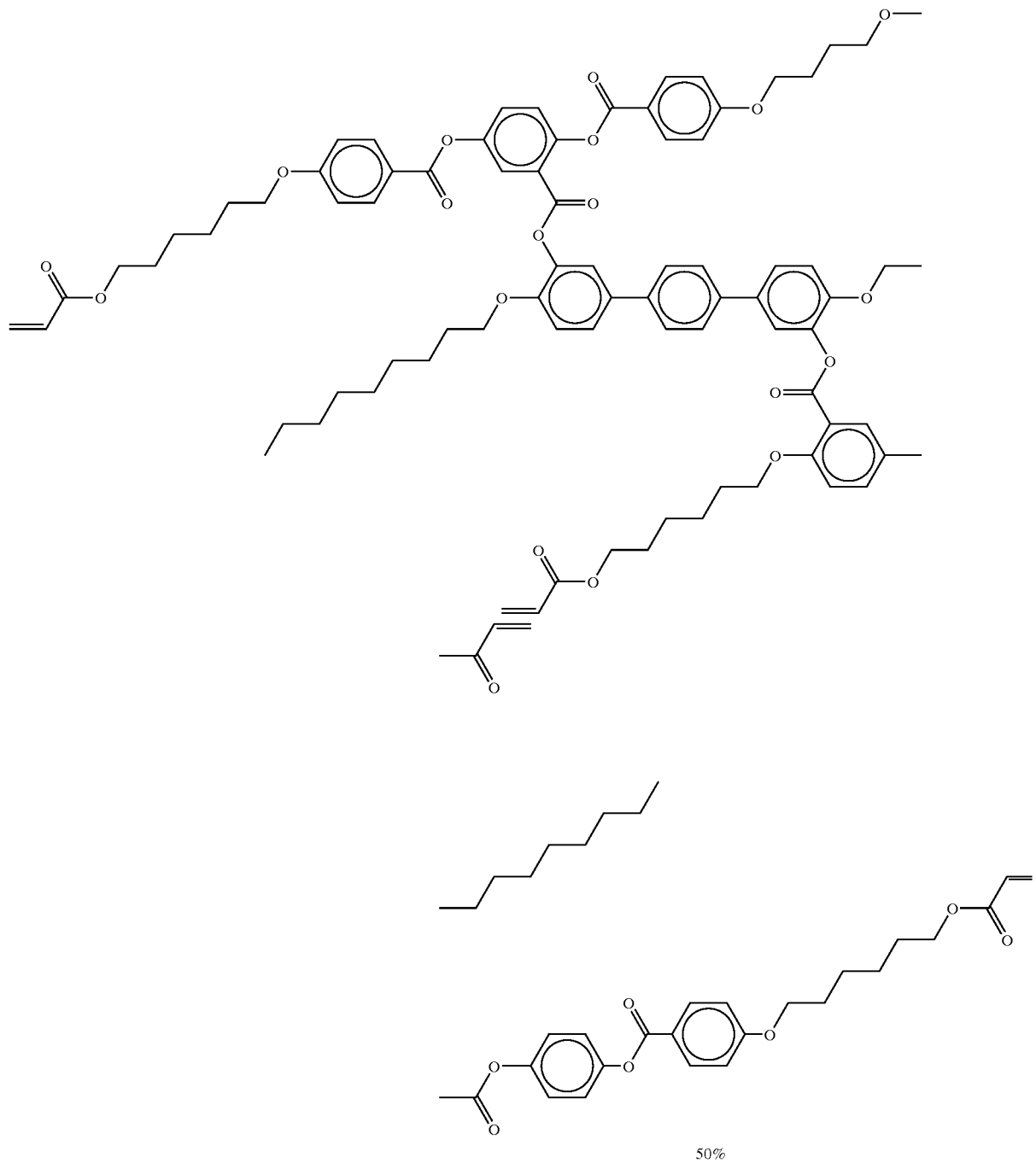

50%

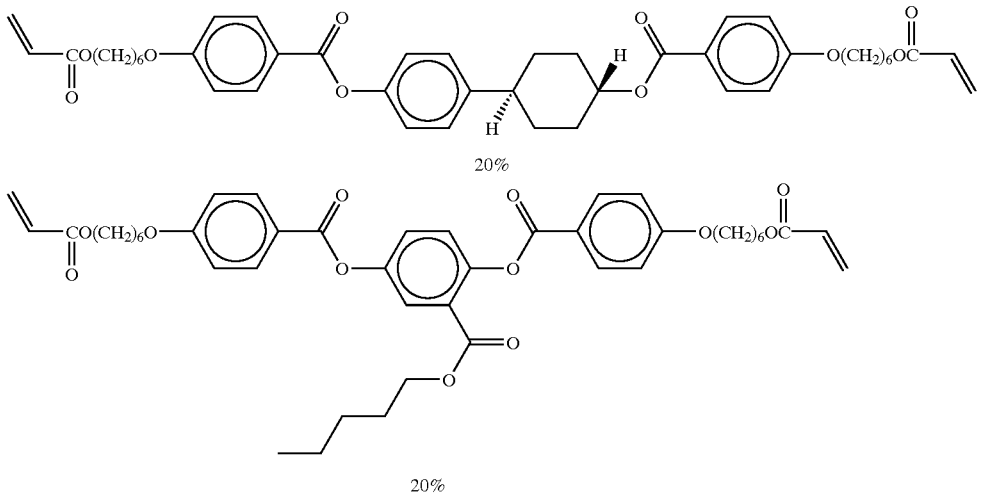

20%

20%

1,4-butanediol diacrylate; Aldrich 10%

To this mixture 500 p.p.m. inhibitor 2,6-di-tert-butyl-4-methylphenol (BHT) is added to prevent premature polymerisation. For the radical photo-polymerisation we use 500 p.p.m. initiator: IRGACURE™ 369 (commercially available from Ciba Geigy, Basle, Switzerland). These mixture were solved in anisole with a ratio of 20:80.

After stirring at room temperature, this mixture were spin-coated on a glass plate with an orientation layer on top to form a layer of ca. 800 nm. This film is then dried at 80° C. for 1 or 2 minutes and photo-polymerised by irradiation with UV light using Mercury lamp for 5 minutes at room temperature in a $N_2$-atmosphere.

The film shows well oriented nematic mesophase with exclusion of any defects. In addition this film exhibits a great tilt angle w.r.t. to plane, as shown by ellipsometric measurements.

What is claimed is:

1. A compound of formula I:

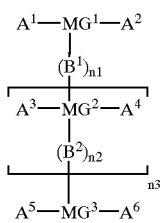

(I)

wherein:

$A^1$ to $A^6$ each independently represent hydrogen; an optionally-substituted methyl group; or an optionally-substituted hydrocarbon group of 2 to 80 C-atoms, in which one or more C-atoms may be replaced by a heteroatom, in such a way that oxygen atoms are not linked to one another;

$B^1$ and $B^2$ each independently represent a single bond, an oxygen atom or an optionally-substituted hydrocarbon group of 1 to 80 C-atoms, in which one or more C-atoms may be replaced by a heteroatom, in such a way that oxygen atoms are not linked to one another;

$MG^1$ and $MG^3$ each independently represent an optionally-substituted aliphatic group with 1 to 80 C-atoms, in which one or more C-atoms may be replaced by a heteroatom, in such a way that oxygen atoms are not linked to one another; or an optionally-substituted aromatic or non-aromatic carbocyclic or heterocyclic ring system, with 1 to 80 C-atoms;

$MG^2$ represents a group comprising at least two and up to four optionally-substituted aromatic or non-aromatic carbocyclic or heterocyclic ring systems, with 1 to 80 C-atoms, wherein, when $MG^2$ represents a group comprising four optionally-substituted ring systems, at least three of the ring systems are aligned in between $B^1$ and $B^2$;

n1 and n2 are each independently 1 or 2, where "n1=2" (or "n2=2") indicates the presence of two separate linkages via the groups $B^1$ (or the groups $B^2$) between the groups $MG^1$ and $MG^2$ (or $MG^2$ and $MG^3$); and n3 is a positive integer up to 1000;

with the proviso that:

when $A^3$ and $A^4$ both represent hydrogen, then both $MG^1$ and $MG^3$ represent an araliphatic group with 1 to 80 C-atoms, in which one or more C-atoms may be replaced by a heteroatom, or an optionally-substituted aromatic or non-aromatic carbocyclic or heterocyclic ring system, with 1 to 80 C-atoms; and at least two of $A^1$, $A^2$, $A^5$ and $A^6$ each independently represent an optionally-substituted hydrocarbon group of 3 to 80 C-atoms, in which one or more C-atoms may be replaced by a heteroatom;

when $A^1$, $A^2$, $A^5$ and $A^6$ all represent hydrogen, then $A^3$ and $A^4$ both represent an optionally-substituted hydrocarbon group of 3 to 80 C-atoms, in which one or more C-atoms may be replaced by a heteroatom; and when $MG^2$ represents a group comprising two or three optionally-substituted ring systems, then neither of $A^3$ and $A^4$ includes an aromatic ring.

2. A compound as claimed in claim 1, wherein at least one of $A^1$ to $A^6$ includes a polymerisable group.

3. A compound as claimed in claim 2, wherein each or any of the groups $A^1$ to $A^6$ is selected from a residue of formula (II):

$$P-(Sp^1)_{k1}-(X^1)_{r1}-$$ (II)

wherein:

P is hydrogen or a polymerisable group selected from groups comprising $CH_2=CW-$, $CH_2=W-O-$, $CH_2=CW-COO-$, $CH_2=C(Ph)-COO-$, $CH_2=CH-COO-Ph-$, $CH_2=CW-CO-NH-$, $CH_2=C(Ph)-CONH-$, $CH_2=C(COOR')-CH_2-COO-$, $CH_2=CH-O-$, $CH_2=CH-OOC-$, $(Ph)-CH=CH-$, $CH_3-C=N-(CH_2)_{m3}-$, $HO-$, $HS-$, $HO-(CH_2)_{m3}-$, $HS-(CH_2)_{m3}-$, $HO(CH_2)_{m3}COO-$, $HS(CH_2)_{m3}COO-$, $HWN-$, $HOC(O)-$, $CH_2=CH-Ph-(O)_{m4}$

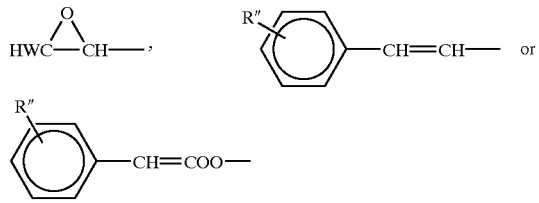

wherein:
W represents H, F, Cl, Br or I or a $C_{1-5}$ alkyl group;
m3 is an integer having a value of from 1 to 9;
m4 is an integer having a value of 0 or 1,
R' represents a $C_{1-5}$ alkyl group; and
R" represents a $C_{1-5}$ alkyl group, methoxy, cyano, F, Cl, Br or I;
$Sp^1$ represents an optionally-substituted $C_{1-20}$ alkylene group, in which one or more C-atoms may be replaced by a heteroatom;
$k^1$ is an integer having a value of from 0 to 4;
$X^1$ represents $-O-$, $-S-$, $-NH-$, $N(CH_3)-$, $-CH(OH)-$, $-CO-$, $-CH_2(CO)-$, $-SO-$, $-CH_2(SO)-$, $-SO_2-$, $-CH_2(SO_2)-$, $-COO-$, $-OCO-$, $-OCO-O-$, $-S-CO-$, $-CO-S-$, $-SOO-$, $-OSO-$, $-SOS-$, $-CH_2-CH_2-$, $-OCH_2-$, $-CH_2O-$, $-CH=CH-$, or $-C\equiv C-$; and
$t^1$ is an integer having a value of 0 or 1;
in which the term Ph denotes phenylene and the term (Ph) denotes phenyl;
with the proviso that at least one of the groups $A^1$ to $A^6$ is not a hydrogen atom.

4. A compound as claimed in claim 3, wherein $A^1$ to $A^6$ each independently represent a group of formula (III):

wherein:
$X^4$ represents $-O-$, $-CO-$, $-COO-$, $-OCO-$, $-C\equiv C-$, or a single bond, especially $-O-$, $-COO-$, $-OCO-$ or single bond;
$Sp^5$ represents a $C_{1-20}$ straight-chain alkylene group, especially ethylene, propylene, butylene, pentylene, hexylene, heptylene, octylene, nonylene, decylene, undecylene, or dodecylene; and
$P^2$ represents hydrogen, $CH_2=CW^5-$ or $CH_2=CW^5-(CO)_{v2}O-$,
wherein:
$W^5$ represents H, $CH_3$, F, Cl, Br or I; and
v2 is 0 or 1.

5. A compound as claimed in claim 1, wherein $B^1$ and/or $B^2$ comprises a group of formula (IV):

wherein:
$Sp^2$ represents a $C_{1-20}$ alkylene group;
$X^2$ and $X^3$ each independently represent $-O-$, $-S-$, $-NH-$, $N(CH_3)-$, $-CH(OH)-$, $-CO-$, $-CH_2(CO)-$, $-SO-$, $-CH_2(SO)-$, $-SO_2-$, $-CH_2(SO_2)-$, $-COO-$, $-OCO-$, $-OCO-O-$, $-S-CO-$, $-CO-S-$, $-SOO-$, $-OSO-$, $-SOS-$, $-CH_2-CH_2-$, $-OCH_2-$, $-CH_2O-$, $-CH=CH-$, $-C\equiv C-$ or a single bond;
$k^2$ is an integer, having a value of 0 or 1;
$t^2$ and $t^3$ are integers, each independently having a value of 0 or 1;
with the proviso that oxygen atoms are not linked one to another.

6. A compound as claimed in claim 5, wherein:
$X^2$ and $X^3$ each independently represent $-O-$, $-CO-$, $-COO-$, $-OCO-$, $-C\equiv C-$, or a single bond; and
$Sp^2$ represents a $C_{1-20}$ straight-chain alkylene group.

7. A compound as claimed in claim 6, wherein $X^2$ and $X^3$ each independently represent $-O-$, $-COO-$, $-OCO-$ or a single bond.

8. A compound as claimed in claim 6, wherein $Sp^2$ represents ethylene, propylene, butylene, pentylene, hexylene, heptylene, octylene, nonylene, decylene, undecylene or dodecylene.

9. A compound as claimed in claim 1, wherein $MG^2$ and at least one of $MG^1$ and $MG^3$ represents a mesogenic group comprising at least two optionally-substituted aromatic or non-aromatic carbocyclic or heterocyclic ring systems.

10. A compound as claimed in claim 1, wherein:
$MG^2$ represents a mesogenic group comprising 2 to 4 aromatic or non-aromatic carbocyclic or heterocyclic ring systems and optionally up to 3 bridging groups; and
at least one of $MG^1$ and $MG^3$ represent a mesogenic group comprising 1 to 4 aromatic or non-aromatic carbocyclic or heterocyclic ring systems and optionally up to 3 bridging groups.

11. A compound as claimed in claim 10, wherein one or more of $MG^1$, $MG^2$ and $MG^3$ represents a mesogenic group selected from the meanings of formulae V:

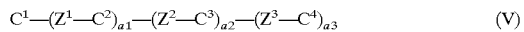

in which:
$C^1$ to $C^4$ are in each case independently optionally-substituted non-aromatic, aromatic, carbocyclic or heterocyclic groups;
$Z^1$ to $Z^3$ are independently from each other $-COO-$, $-OCO-$, $-CH_2-CH_2-$, $-OCH_2-$, $-CH_2O-$, $-CH=CH-$, $-C\equiv C-$, $-CH=CH-COO-$, $-OCO-CH=CH-$ or a single bond; and
a1, a2 and a3 are independently integers 0 to 3, such that $a1+a2+a3 \leq 3$.

12. A compound as claimed in claim 11, wherein $C^1$ to $C^4$ are selected from:

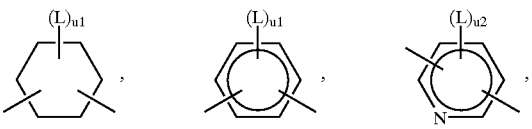

-continued

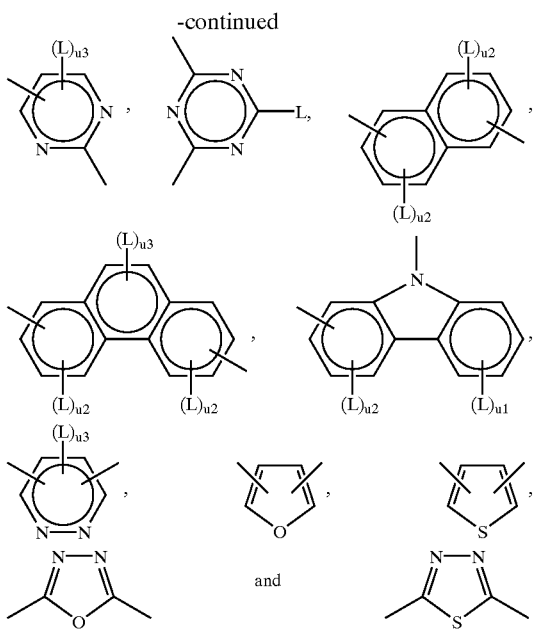

with:

L being —CH$_3$, —COCH$_3$, —NO$_2$, CN, or halogen
u1 being 0, 1, 2, 3, or 4,
u2 being 0, 1, 2, or 3, and
u3 being 0, 1, or 2.

13. A compound as claimed in claim 12, wherein C$^1$ to C$^4$ are selected from cyclohexylene, phenylene, naphthylene or phenanthrylene.

14. A compound as claimed in claim 1, wherein A$^1$ and A$^2$ are identical.

15. A compound as claimed in claim 1, wherein A$^5$ and A$^6$ are identical.

16. A compound as claimed claim 1, wherein A$^1$—MG$^1$—A$^2$ and A$^5$—MG$^3$—A$^6$ are identical.

17. A compound as claimed in claim 1, wherein A$^3$ and A$^4$ are identical.

18. A compound as claimed in claim 1, wherein n1, n2 and n3 equal 1 and B$^1$ and B$^2$ are identical.

19. A liquid crystalline polymer film comprising a compound as claimed in claim 1.

20. A polymer network comprising at least one compound as claimed in claim 1.

21. A polymer network as claimed in claim 20, essentially consisting of:

i) at least one chiral or/and achiral mesogenic polymerisable compound;

ii) at least one "staircase" compound of formula I; and iii) an initiator.

22. A polymer network as claimed in claim 21 further comprising one or more further polymerisable compounds, stabilisers and/or dyes.

23. A liquid crystalline mixture comprising at least one compound as claimed in claim 1.

24. A liquid crystalline polymer film obtainable by polymerisation of a liquid crystalline mixture as claimed in claim 23.

25. A process for the preparation of a liquid crystalline polymer film as claimed in claim 24 comprising the steps of forming the polymerisable liquid crystalline mixture into a thin film, prior to curing.

26. An optical or electro-optical component containing a liquid crystalline polymer film as claimed in claim 24.

* * * * *